(12) United States Patent
Lira et al.

(10) Patent No.: US 10,752,913 B2
(45) Date of Patent: *Aug. 25, 2020

(54) SELECTABLE MARKER GENES

(75) Inventors: Justin M. Lira, Fishers, IN (US);
Terry R. Wright, Carmel, IN (US);
Sean M. Russell, Carmel, IN (US);
Donald J. Merlo, Carmel, IN (US);
Steven R. Webb, Westfield, IN (US);
Nicole L. Arnold, Carmel, IN (US);
Andrew E. Robinson, Brownsburg, IN (US); Kelley A. Smith, Lebanon, IN (US)

(73) Assignee: Dow AgroSciences LLC, Indianapolis, IN (US)

(*) Notice: Subject to any disclaimer, the term of this patent is extended or adjusted under 35 U.S.C. 154(b) by 1611 days.

This patent is subject to a terminal disclaimer.

(21) Appl. No.: 12/517,906

(22) PCT Filed: Dec. 7, 2007

(86) PCT No.: PCT/US2007/086813
§ 371 (c)(1),
(2), (4) Date: Jan. 18, 2011

(87) PCT Pub. No.: WO2008/070845
PCT Pub. Date: Jun. 12, 2008

(65) Prior Publication Data
US 2011/0107455 A1      May 5, 2011

Related U.S. Application Data

(60) Provisional application No. 60/873,602, filed on Dec. 7, 2006.

(51) Int. Cl.
*C12N 15/82* (2006.01)

(52) U.S. Cl.
CPC ..... *C12N 15/8277* (2013.01); *C12N 15/8209* (2013.01)

(58) Field of Classification Search
USPC ........................................................ 800/300
See application file for complete search history.

(56) References Cited

U.S. PATENT DOCUMENTS

| | | | |
|---|---|---|---|
| 5,463,175 A | 10/1995 | Barry et al. | |
| 5,561,236 A * | 10/1996 | Leemans et al. | 800/300 |
| 5,605,793 A | 2/1997 | Stemmer | |
| 5,646,024 A * | 7/1997 | Leemans et al. | 435/6.12 |
| 5,648,477 A * | 7/1997 | Leemans et al. | 536/23.7 |
| 6,284,945 B1 * | 9/2001 | Dudits | A01H 4/00 435/412 |
| 7,250,561 B1 * | 7/2007 | Pallett et al. | 800/300 |
| 7,838,733 B2 * | 11/2010 | Wright et al. | 800/300 |
| 2002/0058249 A1 * | 5/2002 | Subramanian et al. | 435/6 |
| 2003/0041357 A1 | 2/2003 | Jepson et al. | |
| 2006/0277627 A1 | 12/2006 | Wang et al. | |
| 2009/0158469 A1 | 6/2009 | Hasegawa et al. | |

FOREIGN PATENT DOCUMENTS

| | | |
|---|---|---|
| WO | WO 2006/054458 A1 | 11/2004 |
| WO | WO 2005/107437 A2 | 11/2005 |
| WO | WO 2007/053482 A2 | 5/2007 |

OTHER PUBLICATIONS

Bedford et al, Characterization of a gene conferring bialophos resistance in *Streptomyces coelicolor* A3(2), Gene 104 (1), 39-45 (1991); GenBank Accession No. M62753.*
GenBank Accession No. JH0246 (First Published Sep. 10, 1999, characterized as the product of the gene conferring bialophos resistance in *Streptomyces coelicolor* A3(2) by Bedford et al (Gene (1991) 104:39-45)).*
GenBank Accession No. M62753 (Fist Published Apr. 26, 1993, characterized as a gene conferring bialophos resistance in *Streptomyces coelicolor* A3(2) by Bedford et al (Gene (1991) 104:39-45)).*
Bedford et al, Gene (1991) 104:39-45.*
Kohli et al, Plant Mol. Biol. (2003) 52:247-258.*
Bedford, et al., Characterization of a gene conferring bialaphos resistance in *Streptomyces coelicolor* AD(2) gene, 1991, vol. 104, pp. 39-45 (See whole document).
US Environmental Protection Agency Office of Pesticide Programs, Biopesticide registration action document (*Bacillus thuringiensis* Cry1F (Synpro and Cry1Ac(synpro) Construct 281/3006, Insecticidal Crystal Proteins as expressed in cotton, May 2005, p. 10, item 4.
Castle, et al., Discovery and Directed Evolution of a Glyphosate Tolerance Gene, Science, May 2004, vol. 304, p. 1151-1154.
Omura S., et al., Accession BAC 71407 [gi: 29607349], Definition: putative phosphinothricin N_acetyltransferase [*Streptomyces avermitilis*]. NCBI Sequence Revision History [online]; Apr. 7, 2003, url: http://www.ncbi.nlm.nih.gov/entrez/viewer.fcgi?29607349:OLD12:633584 [retrieved Sep. 14, 2010 from URL: httn://www.ncbi.nlm.nih.gov/entrez/sutils/girevhist.cgi?val=BAC71407.

(Continued)

*Primary Examiner* — Mykola V. Kovalenko
(74) *Attorney, Agent, or Firm* — Magleby Cataxinos & Greenwood

(57) ABSTRACT

The subject invention relates to a novel gene referred to herein as DSM-2. This gene was identified in *Sterptomyces coelicolor* A3. The DSM-2 protein is distantly related to PAT and BAR. The subject invention also provides plant-optimized genes encoding DSM-2 proteins, DSM-2 can be used as a transgenic trait to impart tolerance in plants and plant cells to the herbicides glufosinate and bialaphos. One preferred use of the subject genes are as selectable markers. The use of this gene as a selectable marker in a bacterial system can increase efficiency for plant transformations. Use of DSM-2 as the sole selection marker eliminates the need for an additional medicinal antibiotic marker (such as ampicillin resistance) during cloning. Various other uses are also possible according to the subject invention.

16 Claims, 1 Drawing Sheet
Specification includes a Sequence Listing.

(56) References Cited

OTHER PUBLICATIONS

Marcos A. T., et al., Three Genes hrdB, hrdD, and hrdT of Streptomeces griseus IMRU 3570, encoding sigma-factor-like proteins, are differentially expressed under specific nutritional conditions, Gene 1995, vol. 153, p. 41-48. [abstract only].
DeBlock et al.; Engineering herbicide resistance in plants by expression of a detoxifying enzyme; The EMBO Journal vol. 6 No. 9 pp. 2513-2518, 1987.
Davies et al.; I-Methionine Sulfoximine, but Not Phosphinothricin, Is a Substrate for an Acetyltransferase (Gene PA4866) from *Pseudomonas aeruginosa*: Structural and Functional Studies; Biochemistry 2007, 46, 1829-1839.
Fani et al; Analysis of the Inhibitory Concentration of Ammonium Glufosinate in Cotyledons Explants of Tomato Plants (*Solanum lycopersicon*); Biotechnology 11(3): 184-188, 2012.
Thompson et al.; Characterization of the herbicide-resistance gene bar from *Streptomyces hygroscopicus*; The EMBO Journal vol. 6 No. 9 pp. 2519-2523, 1987.
Logusch et al.; Inhibition of Plant Glutamine Synthetases by Substituted Phosphinothricins; Plant Physiol. (1991) 95, 1057-1062.
Manderscheid et al.; Studies on the Mechanism of Inhibition by Phosphinothricin of Glutamine Synthetase Isolated from *Triticum aestivum* L.; J. Plant Physiol. vol. 123; pp. 135-142 (1986).
Segel; Biochemical Calculations: How to Solve Mathematical Problems in General Biochemistry; New York, John Wilery & Sons; 1976; 10 pgs.
Ridley et al.; Effects of Phosphinothricin on the Isoenzymes of Glutamine Synthetase Isolated from Plant Species Which Exhibit Varying Degrees of Susceptibility to the Herbicide; Plant Science, 39 (1985) 31-36.
Acaster et al.; Kinetic analysis of glutamine synthetases from various plants; FEBS 2889; vol. 189, No. 2; Sep. 1985.
Wild et al.; The Effect of Phosphinothricin on the Assimilation of Ammonia in Plants; (1984) Z. Naturforsch 39c, 500-504.
Fraser et al.; Kinetics for glutamine-synthetase inhibition by phosphinothricin and measurement of other enzyme activities in situ in isolated asparagus cells using a freeze-thaw technique; Planta (1984) 161: 470-474.
Faber et al.; Impact of Glufosinate-Ammonium and Bialaphos on the Phytoplankton Community of a Small Eutrophic Northem Lake; Enviommental Toxicology and Chemistry, vol. 17, No. 7, pp. 1282-1290, 1998.
Castle et al.; Discovery and Directed Evolution of a Glyphosate Tolerance Gene; Science vol. 304 May 21, 2004; 1151-1154.
Kaskey; Monsanto Says DuPont Soybeans to Contain Unauthorized Genes; Apr. 7, 2009; Bloomberg News website (www.bloomberg.com).
Stalker et al.; Herbicide Resistance in Transgenic Plants Expressing a Beterial Detoxification Gene; Science 252; 419-423; 1988.
Stlaker et al.; Purification and Properties of a Nitrilase Specific for the Herbicide Bromoxynil and Corresponding Nucleotide Sequence Analysis of the bxn Gene; The Journal of Biological Chemistry; vol. 263; No. 13, Issue of May 5, pp. 6310-6314, 1988.
Harper; Microbial Metabolism of Aromatic Nitriles; Biochem. J. (1977) 165, 309-319.
Harper; Fungal Degradation of Aromatic Nitriles Enzymology of C-N Cleavage by Fusarium Solani; Biochem. J. (1977) 167, 685-692.
Harper; Characterization of Nitrilase From *Nocardia* sp. (Rhodochrous Group) N.C.I.B. 11215, Using p-Hydroxybenzonitrile as sole Carbon Source; Int. J. Biochem. vol. 17, No. 6, pp. 677-683, 1985.
USDA petition for deregulation, 98-216-01p, 1998, available at https://www.aphis.usda.gov/biotechnology/petitions_table_shtml.
Pollegioni et al.; Molecular basis of glyphosate resistance—different approaches through protein engieering; The Febs Journal; 278: 2753-2766; 2011.
Hadi et al.; Glyphosate Tolerance in Transgenic Canola by a Modified Glyphosate Oxidoreductase (gox) Gene; Progress in Biological Sciences vol. 2, No. 1, 50-58 Winter/Spring 2012.
Amrhein et al.; Biochemical basis for glyphosate-tolerance in a bacerium and a plant tissue culture; FEBS 0516; vol. 157, No. 1; Jun. 1983.
Steinrucken et al.; Overproduction of 5-Enolpyruvylshikimate-3-phosphate Synthase in a Glyphosate-Tolerant Petunia hybrida Cell Line; Archives of Biochemistry and Biophysics; vol. 244, No. 1, January, pp. 169-178, 1986.
Botterman et al.; Engineering of Herbicide Resistance in Plants; Biotechnology and Genetic Engineering Reviews; 6(1): 321-40; 2013.
Donn et al.; Herbicide-resistant alfalfa cells: an example of gene amplification in plants; J. Mol. Appl. Genet. 2:621-635 (1984).
Eckes et al.; Overproduction of alfalfa glutamine synthetase in transgenic tobacco plants; Mol Gen Genet (1989) 217: 263-268.
Buttner, et al.; Cloning, Disruption, and Transcriptional Analysis of Three RNA Polymerase Sigma Factor Genes of *Streptomyces coelicolor* A3(2); Journal of Bacteriology, Jun. 1990, p. 3367-3378; vol. 172, No. 6.
Wehrmann, et al.; The similarities of bar and pat gene products make them equally applicable for plant engineers; Nature Biotechnology vol. 14, Oct. 1996; p. 1274-1278.
Baertlein et al., Expression of a Bacterial Ice Nucleation Gene in Plants; Plant Physiol. (1992) 100, 1730-1736.
Comai et al.; Expression in plants of a mutant aroA gene from *Salmonella typhimurium* confers tolerance to glyphosate; Nature vol. 314 Oct. 24, 1985 741-744.
Boros et al.; High-copy-number derivatives of the plasmid cloning vector pBR322; Gene, 30 (1984) 257-260, 4 pgs.
Millan et al.; Multicopy plasmids potentiate the evolution of antibiotic resistance in bacteria; Nature ecology & evolustion; Nov. 7, 2016; vol. 1; Article No. 0010, 8 pgs.
Zaman et al.; Analysis of the site for second-strand initiation during replication of the *Streptomyces plasmid* pIJ101; Journal of General Microbiology (1993), 139, 669-676.

* cited by examiner

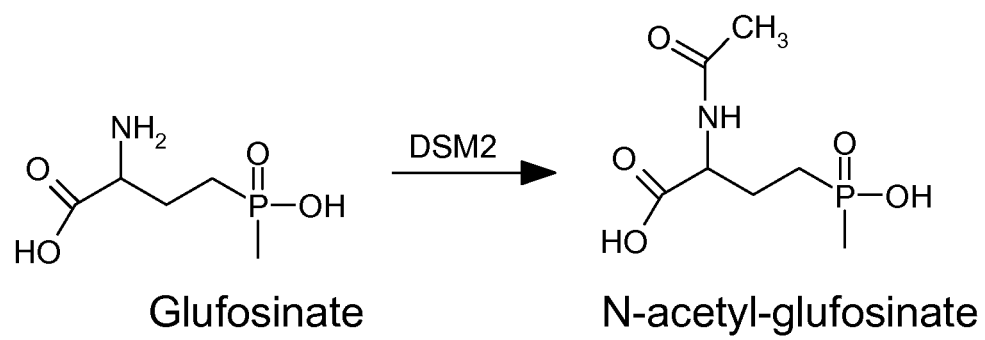

SEQUENCE LISTING

```
<160> NUMBER OF SEQ ID NOS: 10

<210> SEQ ID NO 1
<211> LENGTH: 516
<212> TYPE: DNA
<213> ORGANISM: Streptomyces coelicolor A3

<400> SEQUENCE: 1
atgccgggaa ctgccgaggt ccaggtcaga ccgggagtcg aggaggatct caagccactc        60
accgacctct acaaccacta cgtacgtgag acgcccatca cgttcgacac cgagccgttc       120
actccggagg agcgccgacc gtggctgctc tcccaccctg aagacggccc gtaccgcctg       180
agggttgcca cggacgcgga gtcacaggag atcctggggt acgccacatc cagccctac        240 cgcgcgaagc ccgcctacgc gacctcggtg gagaccaccg tctacgtcgc ccgggggcc         300 ggcggccgcg gcatcggctc gctcctctac gcgtccctct tcgacgccct ggccgccgag       360
gacctgcacc gcgcctacgc gggcatcgcc cagcccaacg aggcctccgc ccggctgcac       420
```

```
gcgcgcttcg gtttccggca cgtgggcacg taccgcgagg tgggccgcaa gttcggccgg    480
tactgggacg tggcctggta cgagagaccg ctctag                               516
```

<210> SEQ ID NO 2
<211> LENGTH: 171
<212> TYPE: PRT
<213> ORGANISM: Streptomyces coelicolor A3

<400> SEQUENCE: 2

```
Met Pro Gly Thr Ala Glu Val Gln Val Arg Pro Gly Val Glu Glu Asp
1               5                   10                  15

Leu Lys Pro Leu Thr Asp Leu Tyr Asn His Tyr Val Arg Glu Thr Pro
            20                  25                  30

Ile Thr Phe Asp Thr Glu Pro Phe Thr Pro Glu Glu Arg Arg Pro Trp
        35                  40                  45

Leu Leu Ser His Pro Glu Asp Gly Pro Tyr Arg Leu Arg Val Ala Thr
    50                  55                  60

Asp Ala Glu Ser Gln Glu Ile Leu Gly Tyr Ala Thr Ser Ser Pro Tyr
65                  70                  75                  80

Arg Ala Lys Pro Ala Tyr Ala Thr Ser Val Glu Thr Thr Val Tyr Val
                85                  90                  95

Ala Pro Gly Ala Gly Gly Arg Gly Ile Gly Ser Leu Leu Tyr Ala Ser
            100                 105                 110

Leu Phe Asp Ala Leu Ala Ala Glu Asp Leu His Arg Ala Tyr Ala Gly
        115                 120                 125

Ile Ala Gln Pro Asn Glu Ala Ser Ala Arg Leu His Ala Arg Phe Gly
    130                 135                 140

Phe Arg His Val Gly Thr Tyr Arg Glu Val Gly Arg Lys Phe Gly Arg
145                 150                 155                 160

Tyr Trp Asp Val Ala Trp Tyr Glu Arg Pro Leu
                165                 170
```

<210> SEQ ID NO 3
<211> LENGTH: 516
<212> TYPE: DNA
<213> ORGANISM: Streptomyces coelicolor A3

<400> SEQUENCE: 3

```
atgcctggaa ctgctgaggt ccaagttcgc cctggagtcg aagaggacct caaaccactc    60
accgatctct acaaccacta cgttcgtgag actccaataa cctttgacac tgagccattc   120
actccagaag agcgtaggcc ttggcttttg agccacccag aagatggccc ttataggttg   180
agggttgcca ccgatgcaga gtcccaagaa atccttggct acgccacctc aagcccctac   240
agagccaagc cagcatacgc aacctctgtg gaaacaacag tctatgttgc ccctggtgct   300
ggtggacgtg gaattgggtc tctccttat gcctccctct ttgacgccct gctgccgag    360 gaccttcaca gagcttatgc tggcatcgct cagcccaatg aggcatcagc acgcttgcat   420
gctaggtttg gtttcagaca tgtgggcact taccgcgaag tggggaggaa gtttggtcgt   480
tactgggatg tggcttggta tgagagaccc ttgtga                             516
```

<210> SEQ ID NO 4
<211> LENGTH: 171
<212> TYPE: PRT
<213> ORGANISM: Streptomyces coelicolor A3

<400> SEQUENCE: 4

```
Met Pro Gly Thr Ala Glu Val Gln Val Arg Pro Gly Val Glu Glu Asp
1               5                   10                  15

Leu Lys Pro Leu Thr Asp Leu Tyr Asn His Tyr Val Arg Glu Thr Pro
            20                  25                  30

Ile Thr Phe Asp Thr Glu Pro Phe Thr Pro Glu Glu Arg Arg Pro Trp
        35                  40                  45

Leu Leu Ser His Pro Glu Asp Gly Pro Tyr Arg Leu Arg Val Ala Thr
    50                  55                  60

Asp Ala Glu Ser Gln Glu Ile Leu Gly Tyr Ala Thr Ser Ser Pro Tyr
65                  70                  75                  80

Arg Ala Lys Pro Ala Tyr Ala Thr Ser Val Glu Thr Thr Val Tyr Val
                85                  90                  95

Ala Pro Gly Ala Gly Gly Arg Gly Ile Gly Ser Leu Leu Tyr Ala Ser
            100                 105                 110

Leu Phe Asp Ala Leu Ala Ala Glu Asp Leu His Arg Ala Tyr Ala Gly
        115                 120                 125

Ile Ala Gln Pro Asn Glu Ala Ser Ala Arg Leu His Ala Arg Phe Gly
    130                 135                 140

Phe Arg His Val Gly Thr Tyr Arg Glu Val Gly Arg Lys Phe Gly Arg
145                 150                 155                 160

Tyr Trp Asp Val Ala Trp Tyr Glu Arg Pro Leu
                165                 170
```

<210> SEQ ID NO 5
<211> LENGTH: 24
<212> TYPE: DNA
<213> ORGANISM: Artificial Sequence
<220> FEATURE:
<223> OTHER INFORMATION: Forward PTU primer "MAS123"

<400> SEQUENCE: 5
gaacagttag acatggtcta aagg                                          24

<210> SEQ ID NO 6
<211> LENGTH: 27
<212> TYPE: DNA
<213> ORGANISM: Artificial Sequence
<220> FEATURE:
<223> OTHER INFORMATION: reverse PTU primer "Per5-4"

<400> SEQUENCE: 6
gctgcaacac tgataaatgc caactgg                                       27

<210> SEQ ID NO 7
<211> LENGTH: 22
<212> TYPE: DNA
<213> ORGANISM: Artificial Sequence
<220> FEATURE:
<223> OTHER INFORMATION: forward coding region primer

<400> SEQUENCE: 7
atggctcatg ctgccctcag cc                                            22

<210> SEQ ID NO 8
<211> LENGTH: 22
<212> TYPE: DNA
<213> ORGANISM: Artificial Sequence
<220> FEATURE:
<223> OTHER INFORMATION: reverse coding region primer

<400> SEQUENCE: 8

-continued

```
cgggcaggcc taactccacc aa                                              22

<210> SEQ ID NO 9
<211> LENGTH: 21
<212> TYPE: DNA
<213> ORGANISM: Artificial Sequence
<220> FEATURE:
<223> OTHER INFORMATION: Forward primer for Coding Region PCR for DSM-2

<400> SEQUENCE: 9
atgcctggaa ctgctgaggt c                                               21

<210> SEQ ID NO 10
<211> LENGTH: 21
<212> TYPE: DNA
<213> ORGANISM: Artificial Sequence
<220> FEATURE:
<223> OTHER INFORMATION: Reverse primer for Coding Region PCR for DSM-2

<400> SEQUENCE: 10
tgagcgatgc cagcataagc t                                               21
```

SELECTABLE MARKER GENES

This application is a National Stage filing of PCT International Application Serial No. PCT/US2007/86813, filed Dec. 7, 2007, which claims the benefit of U.S. Provisional Application Ser. No. 60/873,602, filed Dec. 7, 2006, the disclosures each of which are expressly incorporated herein by reference.

BACKGROUND OF THE INVENTION

A selectable marker is a detectable genetic trait or segment of DNA that can be identified and tracked. A marker gene typically serves as a flag for another gene, sometimes called the target gene. A marker gene is typically used with a target gene being used to transform target cells. Target cells that heritably receive the target gene can be identified by selecting for cells that also express the marker gene. The marker gene is near enough to the target gene so that the two genes (the marker gene and the target gene) are genetically linked and are usually inherited together. The current standard for selectable markers is the "pat" gene which encodes an enzyme called phosphinothricin acetyl transferase.

Glutamine synthetase ("GS") in many plants is an essential enzyme for the development and life of plant cells. GS converts glutamate into glutamine. GS is also involved in ammonia assimilation and nitrogen metabolism. GS is involved in a pathway in most plants for the detoxification of ammonia released by nitrate reduction. Therefore, potent inhibitors of GS are very toxic to plant cells. Breakdown or modification of the herbicide inside the plant could lead to resistance.

A particular class of herbicides has been developed, based on the toxic effect due to inhibition of GS in plants. Bialaphos and phosphinothricin are two such inhibitors of the action of GS and possess excellent herbicidal properties. These two herbicides are non-selective; they inhibit growth of all the different species of plants present on the soil, accordingly causing their total destruction.

Bialaphos is also a broad spectrum herbicide. Bialaphos is composed of phosphinothricin (PPT or PTC; 2-amino-4-methylphosphinobutyric acid), an analogue of L-glutamic acid, and two L-alanine residues. Thus the structural difference between PPT and Bialaphos resides in the absence of two alanine amino acids in the case of PPT. Upon removal of the L-alanine residues of Bialaphos by intracellular peptidases, the PPT is released. PPT is a potent inhibitor of GS. Inhibition of GS in plants by PPT causes the rapid accumulation of ammonia and death of the plant cells.

Bialaphos was first disclosed as having antibiotic properties, which enabled it to be used as a pesticide or a fungicide. U.S. Pat. No. 3,832,394 relates to cultivating *Streptomyces hygroscopicus*, and recovering Bialaphos from its culture media. However, other strains, such as *Streptomyces viridochromogenes*, also produce this compound. Other tripeptide antibiotics which contain a PPT moiety are also known to exist in nature, such as phosalacin. PPT is also obtained by chemical synthesis and is commercially distributed.

Bialaphos-producing *Streptomyces hygroscopicus* and *Streptomyces viridochromogenes* are protected from PPT toxicity by an enzyme with phosphinothricin acetyl transferase activity. Plant Physiol, April 2001, Vol. 125, pp. 1585-1590 ("Expression of bar in the Plastid Genome Confers Herbicide Resistance," Lutz et al.). The *Streptomyces* species that produce these antibiotics would themselves be destroyed if they did not have a self-defense mechanism against these antibiotics. This self-defense mechanism has been found in several instances to comprise an enzyme capable of inhibiting the antibiotic effect.

Phosphinothricin acetyl transferase is encoded by either the bar (bialaphos resistance; Thompson et al., 1987) or pat (phosphinothricin acetyltransferase; Strauch et al., 1988) genes, and detoxifies PPT by acetylation of the free amino group of PPT. The enzymes encoded by these two genes are functionally identical and show 85% identity at the amino acid level (Wohlleben et al., 1988; Wehrmann et al., 1996). PPT-resistant crops have been obtained by expressing chimeric bar or pat genes in the cytoplasm from nuclear genes. Herbicide-resistant lines have been obtained by direct selection for PPT resistance in tobacco (*Nicotiana tabacum* cv Petit Havana), potato, *Brassica napus, Brassica oleracea* (De Block et al., 1987; De Block et al., 1989), maize (Spencer et al., 1990), and rice (Cao et al., 1992).

A gene (bar) was identified adjacent to the hrdD sigma factor gene in *Streptomyces coelicolor* A3. The predicted bar product showed 32.2% and 30.4% identity to those of the pat and bar genes of the bialaphos producers *Streptomyces viridochromogenes* and *Streptomyces hygroscopicus*, respectively. The *S. coelicolor* bar gene conferred resistance to bialaphos when cloned in *S. coelicolor* on a high-copy-number vector. Bedford et al., Gene, 1991 Jul. 31; 104(1): 39-45, "Characterization of a gene conferring bialaphos resistance in *Streptomyces coelicolor* A3(2)." Heterologous expression of this gene in other microbes, or transformation of this gene into plants, has not heretofore been reported.

The use of the herbicide resistance trait is referred to in DE 3642 829 A and U.S. Pat. No. 5,879,903 (as well as U.S. Pat. Nos. 5,637,489; 5,276,268; and 5,273,894) wherein the pat gene is isolated from *Streptomyces viridochromogenes*. WO 87/05629 and U.S. Pat. No. 5,648,477 (as well as U.S. Pat. Nos. 5,646,024 and 5,561,236) refer to the use of the bar gene from *S. hygroscopiicus* for protecting plant cells and plants from glutamine synthetase inhibitors (such as PPT) and to the development of herbicide resistance in the plants. The gene encoding resistance to the herbicide BASTA (Hoechst phosphinothricin) or Herbiace (Meiji Seika bialaphos) was introduced by *Agrobacterium* infection into tobacco (*Nicotiana tabacum* cv Petit Havan SRI), potato (*Solanum tuberosum* cv Benolima), and tomato (*Lycopersicum esculentum*) plants, and conferred herbicide resistance.

BRIEF SUMMARY OF THE INVENTION

The subject invention relates to a novel gene referred to herein as DSM-2. This gene was identified in *Sterptomyces coelicolor* (A3). The DSM-2 protein is distantly related to PAT and BAR. The subject invention also provides plant-optimized genes encoding DSM-2 proteins. DSM-2 can be used as a transgenic trait to impart tolerance in microorganisms, plant cells, and plants to the herbicidal and antibacterial molecules, glufosinate, phosphinothricin, and/or bialaphos.

Transformation into *Arabidopsis* allows recovery at high rates of glufosinate. Once introduced, the DSM-2 gene has the capability to provide significant selection and whole plant resistance.

There is high inherent value for the subject genes simply as a selectable marker for biotechnology projects. In some preferred embodiments, the subject genes can be used as markers for selecting successfully transformed cells in culture, and whole plants in the greenhouse, and field. This gene and similar homologues can be used in place of pat and/or bar.

The use of this gene as a selectable marker in a bacterial transformation system can increase efficiency for all plant transformations. Use of DSM-2 as the sole selection marker eliminates the need for an additional medicinal antibiotic marker (such as ampicillin resistance) during cloning.

Various other uses are also possible according to the subject invention. DSM-2 can be useful as a transgenic trait to impart tolerance to plants to the herbicides glufosinate and bialaphos.

This gene can also be used as the basis for a novel, plant-transformation system in conjunction with a modified *Agrobacterium* strain. Novel strains of *Pseudomonas fluorescens*, or other microbial strains, used for protein production and incorporating non-medicinal antibiotic resistance marker genes can also be produced according to the subject invention. Improvement in cloning and transformation processes and efficiency, by elimination of fragment purification away from medicinal antibiotic resistance elements can also be a benefit.

In addition to herbicide tolerant crop (HTC) traits, methods for controlling weeds using herbicides for which herbicide tolerance is created by the subject genes in transgenic crops is also within the scope of the subject invention. Combination of the subject HTC trait is also beneficial when combined with other HTC traits (including but not limited to glyphosate tolerance and 2,4-D tolerance), particularly for controlling species with newly acquired resistance or inherent tolerance to a herbicide (such as glyphosate). In addition, when rotating glyphosate tolerant crops (which are becoming increasingly prevalent worldwide) with other glyphosate tolerant crops, control of glyphosate resistant volunteers may be difficult. Thus, use of these transgenic traits stacked or transformed individually into crops may provide a tool for control of other HTC volunteer crops.

BRIEF DESCRIPTION OF THE FIGURES

FIG. 1: shows deactivation of glufosinate by N-acetylation mediated by DSM2.

BRIEF DESCRIPTION OF THE SEQUENCES

SEQ ID NO:1 is the Native DSM-2 sequence.
SEQ ID NO:2 is the Native Protein sequence.
SEQ ID NO:3 is the Hemicot DSM-2 (v2) sequence.
SEQ ID NO:4 is the Rebuilt Protein sequence.
SEQ ID NO:5 is the Pat PTU primer (MAS 123).
SEQ ID NO:6 is the Pat PTU primer (Per 5-4).
SEQ ID NO:7 is the Pat coding region primer
SEQ ID NO:8 is the Pat coding region primer
SEQ ID NO:9 is the DSM-2 (v2) coding region primer
SEQ ID NO:10 is the DSM-2 (v2) coding region primer

DETAILED DESCRIPTION OF THE INVENTION

The subject invention relates to a novel gene referred to herein as DSM-2. This gene was identified in *Sterptomyces coelicolor* (A3). The DSM-2 protein is distantly related to PAT and BAR (30 and 28% amino acid identity, respectively). The subject invention also provides plant-optimized genes, encoding the DSM-2 proteins, with a hemicot bias for example. DSM-2 can be used as a transgenic trait to impart tolerance in plants and plant cells to the herbicides glufosinate, phosphinothricin, and bialaphos.

There is high inherent value for the subject genes simply as a selectable marker for biotechnology projects. However, various other uses are also possible according to the subject invention.

DSM-2 can be useful as a transgenic trait to impart tolerance to plants to the herbicides glufosinate, phosphinothricin, and bialaphos.

In some preferred embodiments, (separate from or in addition to herbicide tolerant crops—HTC) is as a selectable marker for selecting successfully transformed cells and whole plants in culture, greenhouse, and in the field. This gene and similar homologues can be used in place of pat and/or bar. One embodiment exemplified herein is the use of DSM-2 as a selectable marker in NT-1 tobacco cells. The subject genes can also be used as selectable markers in other plant systems such as corn and rice.

The use of this gene as a selectable marker in a bacterial system can increase efficiency for all plant transformations. Use of DSM-2 as the sole selection marker eliminates the need for an additional medicinal antibiotic marker (such as ampicillin resistance) during cloning.

Experiments demonstrated that the *Escherichia coli* cell line BL21—Star (DE3) (Invitrogen catalog # C6010-03) was inhibited on minimal media containing concentrations of 100 µg/ml of glufosinate ammonium (Basta). The expression of DSM-2 in the BL21 Star cell line complemented resistance on minimal media containing 400 µg/ml of glufosinate. These experiments indicate that the expression of DSM-2 can be used as a non-medicinal antibiotic selectable marker for cloning applications in bacteria that are inhibited by glufosinate.

Further experiments demonstrated that the plant promoters *Arabidopsis thaliana* PolyUbiquitin 10 (At Ubi10) and the viral promoter Cassava Vein Mosaic Virus (CsVMV) are functional in the *E. coli* strain BL21—Star (DE3). Both promoters expressed adequate DSM-2 protein to provide resistance to minimal media containing 200 µg/ml of glufosinate. These plant promoters can be used to drive the expression of DSM-2 as a non-medicinal antibiotic selectable marker in *E. coli*. Functionality of a single plant promoter in both bacteria and plants eliminates the requirement of separate selectable markers for each species.

This gene can also be used as the basis for a novel, plant-transformation system in conjunction with a modified *Agrobacterium* strain. Novel strains of *Pseudomonas fluorescens*, or other microbial strains, for protein production using non-medicinal antibiotic resistance marker genes can also be produced according to the subject invention. Improvement in cloning and transformation processes and efficiency by elimination of fragment purification, away from medicinal antibiotic resistance elements can also be a benefit.

In addition to HTC traits, methods for controlling weeds using herbicides for which herbicide tolerance is created by the subject genes in transgenic crops is also within the scope of the subject invention. Combination of the subject HTC trait is also beneficial when combined with other HTC traits (including but not limited to glyphosate tolerance and 2,4-D tolerance), particularly for controlling species with newly acquired resistance or inherent tolerance to a herbicide (such as glyphosate). In addition, when rotating glyphosate tolerant crops (which are becoming increasingly prevalent worldwide) with other glyphosate tolerant crops, control of glyphosate resistant volunteers may be difficult. Thus, use of these transgenic traits stacked or transformed individually into crops may provide a tool for control of other HTC volunteer crops.

Proteins (and Source Isolates) of the Subject Invention.

The present invention provides functional proteins. By "functional activity" (or "active") it is meant herein that the proteins/enzymes for use according to the subject invention have the ability to degrade or diminish the activity of a herbicide (alone or in combination with other proteins). Plants producing proteins of the subject invention will preferably produce "an effective amount" of the protein so that when the plant is treated with a herbicide, the level of protein expression is sufficient to render the plant completely or partially resistant or tolerant to the herbicide (at a typical rate, unless otherwise specified; typical application rates can be found in the well-known *Herbicide Handbook* (Weed Science Society of America, Eighth Edition, 2002), for example). The herbicide can be applied at rates that would normally kill the target plant, at normal field use rates and concentrations. (Because of the subject invention, the level and/or concentration can optionally be higher than those that were previously used.) Preferably, plant cells and plants of the subject invention are protected against growth inhibition or injury caused by herbicide treatment. Transformed plants and plant cells of the subject invention are preferably rendered resistant or tolerant to an herbicide, as discussed herein, meaning that the transformed plant and plant cells can grow in the presence of effective amounts of one or more herbicides as discussed herein. Preferred proteins of the subject invention have catalytic activity to metabolize one or more aryloxyalkanoate compounds. One cannot easily discuss the term "resistance" and not use the verb "tolerate" or the adjective "tolerant." The industry has spent innumerable hours debating Herbicide Tolerant Crops (HTC) versus Herbicide Resistant Crops (HRC). HTC is a preferred term in the industry. However, the official Weed Science Society of America definition of resistance is "the inherited ability of a plant to survive and reproduce following exposure to a dose of herbicide normally lethal to the wild type. In a plant, resistance may be naturally occurring or induced by such techniques as genetic engineering or selection of variants produced by tissue culture or mutagenesis." As used herein unless otherwise indicated, herbicide "resistance" is heritable and allows a plant to grow and reproduce in the presence of a typical herbicidally effective treatment by a herbicide for a given plant, as suggested by the current edition of *The Herbicide Handbook* as of the filing of the subject disclosure. As is recognized by those skilled in the art, a plant may still be considered "resistant" even though some degree of plant injury from herbicidal exposure is apparent. As used herein, the term "tolerance" is broader than the term "resistance," and includes "resistance" as defined herein, as well an improved capacity of a particular plant to withstand the various degrees of herbicidally induced injury that typically result in wild-type plants of the same genotype at the same herbicidal dose.

Transfer of the functional activity to plant or bacterial systems can involve a nucleic acid sequence, encoding the amino acid sequence for a protein of the subject invention, integrated into a protein expression vector appropriate to the host in which the vector will reside. One way to obtain a nucleic acid sequence encoding a protein with functional activity is to isolate the native genetic material from the bacterial species which produce the protein of interest, using information deduced from the protein's amino acid sequence, as disclosed herein. The native sequences can be optimized for expression in plants, for example, as discussed in more detail below. An optimized polynucleotide can also be designed based on the protein sequence.

One way to characterize these classes of proteins and the polynucleotides that encode them is by defining a polynucleotide by its ability to hybridize, under a range of specified conditions, with an exemplified nucleotide sequence (the complement thereof and/or a probe or probes derived from either strand) and/or by their ability to be amplified by PCR using primers derived from the exemplified sequences.

There are a number of methods for obtaining proteins for use according to the subject invention. For example, antibodies to the proteins disclosed herein can be used to identify and isolate other proteins from a mixture of proteins. Specifically, antibodies may be raised to the portions of the proteins that are most conserved or most distinct, as compared to other related proteins. These antibodies can then be used to specifically identify equivalent proteins with the characteristic activity by immunoprecipitation, enzyme linked immunosorbent assay (ELISA), or immuno-blotting. Antibodies to the proteins disclosed herein, or to equivalent proteins, or to fragments of these proteins, can be readily prepared using standard procedures. Such antibodies are an aspect of the subject invention. Antibodies of the subject invention include monoclonal and polyclonal antibodies, preferably produced in response to an exemplified or suggested protein.

With the benefits of the subject disclosure, proteins and genes of the subject invention can be obtained from a variety of sources, including a variety of microorganisms such as recombinant and/or wild-type bacteria, for example.

Mutants of bacterial isolates can be made by procedures that are well known in the art. For example, asporogenous mutants can be obtained through ethylmethane sulfonate (EMS) mutagenesis of an isolate. The mutants can be made using ultraviolet light and nitrosoguanidine by procedures well known in the art.

A protein "from" or "obtainable from" any of the subject isolates referred to or suggested herein means that the protein (or a similar protein) can be obtained from the isolate or some other source, such as another bacterial strain or a plant. "Derived from" also has this connotation, and includes proteins obtainable from a given type of bacterium that are modified for expression in a plant, for example. One skilled in the art will readily recognize that, given the disclosure of a bacterial gene and protein, a plant can be engineered to produce the protein. Antibody preparations, nucleic acid probes (DNA, RNA, or PNA, for example), and the like can be prepared using the polynucleotide and/or amino acid sequences disclosed herein and used to screen and recover other related genes from other (natural) sources.

Standard molecular biology techniques may be used to clone and sequence the proteins and genes described herein. Additional information may be found in Sambrook et al., 1989, which is incorporated herein by reference.

Polynucleotides and Probes.

The subject invention further provides nucleic acid sequences that encode proteins for use according to the subject invention. The subject invention further provides methods of identifying and characterizing genes that encode proteins having the desired herbicidal activity. In one embodiment, the subject invention provides unique nucleotide sequences that are useful as hybridization probes and/or primers for PCR techniques. The primers produce characteristic gene fragments that can be used in the identification, characterization, and/or isolation of specific genes of interest. The nucleotide sequences of the subject invention encode proteins that are distinct from previously described proteins.

The polynucleotides of the subject invention can be used to form complete "genes" to encode proteins or peptides in a desired host cell. For example, as the skilled artisan would readily recognize, the subject polynucleotides can be appropriately placed under the control of a promoter in a host of interest, as is readily known in the art. The level of gene expression and temporal/tissue specific expression can greatly impact the utility of the invention. Generally, greater levels of protein expression of a degradative gene will result in faster and more complete degradation of a substrate (in this case a target herbicide). Promoters will be desired to express the target gene at high levels unless the high expression has a consequential negative impact on the health of the plant. Typically, one would wish to have the DSM-2 gene constitutively expressed in all tissues for complete protection of the plant at all growth stages. However, one could alternatively use a vegetatively expressed resistance gene; this would allow use of the target herbicide in-crop for weed control and would subsequently control sexual reproduction of the target crop by application during the flowering stage.

As the skilled artisan knows, DNA typically exists in a double-stranded form. In this arrangement, one strand is complementary to the other strand and vice versa. As DNA is replicated in a plant (for example), additional complementary strands of DNA are produced. The "coding strand" is often used in the art to refer to the strand that binds with the anti-sense strand. The mRNA is transcribed from the "anti-sense" strand of DNA. The "sense" or "coding" strand has a series of codons (a codon is three nucleotides that can be read as a three-residue unit to specify a particular amino acid) that can be read as an open reading frame (ORF) to form a protein or peptide of interest. In order to produce a protein in vivo, a strand of DNA is typically transcribed into a complementary strand of mRNA which is used as the template for the protein. Thus, the subject invention includes the use of the exemplified polynucleotides shown in the attached sequence listing and/or equivalents including the complementary strands. RNA and PNA (peptide nucleic acids) that are functionally equivalent to the exemplified DNA molecules are included in the subject invention.

In one embodiment of the subject invention, bacterial isolates can be cultivated under conditions resulting in high multiplication of the microbe. After treating the microbe to provide single-stranded genomic nucleic acid, the DNA can be contacted with the primers of the invention and subjected to PCR amplification. Characteristic fragments of genes of interest will be amplified by the procedure, thus identifying the presence of the gene(s) of interest.

Further aspects of the subject invention include genes and isolates identified using the methods and nucleotide sequences disclosed herein. The genes thus identified can encode herbicidal resistance proteins of the subject invention.

Proteins and genes for use according to the subject invention can be identified and obtained by using oligonucleotide probes, for example. These probes are detectable nucleotide sequences that can be detectable by virtue of an appropriate label or may be made inherently fluorescent as described in International Application No. WO 93/16094. The probes (and the polynucleotides of the subject invention) may be DNA, RNA, or PNA. In addition to adenine (A), cytosine (C), guanine (G), thymine (T), and uracil (U; for RNA molecules), synthetic probes (and polynucleotides) of the subject invention can also have inosine (a neutral base capable of pairing with all four bases; sometimes used in place of a mixture of all four bases in synthetic probes) and/or other synthetic (non-natural) bases. Thus, where a synthetic, degenerate oligonucleotide is referred to herein, and "N" or "n" is used generically, "N" or "n" can be G, A, T, C, or inosine. Ambiguity codes as used herein are in accordance with standard IUPAC naming conventions as of the filing of the subject application (for example, R means A or G, Y means C or T, etc.).

As is well known in the art, if a probe molecule hybridizes with a nucleic acid sample, it can be reasonably assumed that the probe and sample have substantial homology/similarity/identity. Preferably, hybridization of the polynucleotide is first conducted followed by washes under conditions of low, moderate, or high stringency by techniques well-known in the art, as described in, for example, Keller, G. H., M. M. Manak (1987) *DNA Probes*, Stockton Press, New York, N.Y., pp. 169-170. For example, as stated therein, low stringency conditions can be achieved by first washing with 2×SSC (Standard Saline Citrate)/0.1% SDS (Sodium Dodecyl Sulfate) for 15 minutes at room temperature. Two washes are typically performed. Higher stringency can then be achieved by lowering the salt concentration and/or by raising the temperature. For example, the wash described above can be followed by two washings with 0.1×SSC/0.1% SDS for 15 minutes each at room temperature followed by subsequent washes with 0.1×SSC/0.1% SDS for 30 minutes each at 55° C. These temperatures can be used with other hybridization and wash protocols set forth herein and as would be known to one skilled in the art (SSPE can be used as the salt instead of SSC, for example). The 2×SSC/0.1% SDS can be prepared by adding 50 ml of 20×SSC and 5 ml of 10% SDS to 445 ml of water. 20×SSC can be prepared by combining NaCl (175.3 g/0.150 M), sodium citrate (88.2 g/0.015 M), and water, adjusting pH to 7.0 with 10 N NaOH, then adjusting the volume to 1 liter. 10% SDS can be prepared by dissolving 10 g of SDS in 50 ml of autoclaved water, then diluting to 100 ml.

Detection of the probe provides a means for determining in a known manner whether hybridization has been maintained. Such a probe analysis provides a rapid method for identifying genes of the subject invention. The nucleotide segments used as probes according to the invention can be synthesized using a DNA synthesizer and standard procedures. These nucleotide sequences can also be used as PCR primers to amplify genes of the subject invention.

Hybridization characteristics of a molecule can be used to define polynucleotides of the subject invention. Thus the subject invention includes polynucleotides (and/or their complements, preferably their full complements) that hybridize with a polynucleotide exemplified herein. That is, one way to define a gene (and the protein it encodes), for example, is by its ability to hybridize (under any of the conditions specifically disclosed herein) with a known or specifically exemplified gene.

As used herein, "stringent" conditions for hybridization refers to conditions which achieve the same, or about the same, degree of specificity of hybridization as the conditions employed by the current applicants. Specifically, hybridization of immobilized DNA on Southern blots with $^{32}$P-labeled gene-specific probes can be performed by standard methods (see, e.g., Maniatis et al. 1982). In general, hybridization and subsequent washes can be carried out under conditions that allow for detection of target sequences. For double-stranded DNA gene probes, hybridization can be carried out overnight at 20-25° C. below the melting temperature (Tm) of the DNA hybrid in 6×SSPE, 5×Denhardt's solution, 0.1% SDS, 0.1 mg/ml denatured DNA. The melting temperature is described by the following formula (Beltz et al. 1983):

$$Tm = 81.5° C. + 16.6 \text{ Log } [Na+] + 0.41(\% G+C) - 0.61(\% \text{ formamide}) - 600/\text{length of duplex in base pairs}.$$

Washes can typically be carried out as follows:
(1) Twice at room temperature for 15 minutes in 1×SSPE, 0.1% SDS (low stringency wash).
(2) Once at Tm-20° C. for 15 minutes in 0.2×SSPE, 0.1% SDS (moderate stringency wash).

For oligonucleotide probes, hybridization can be carried out overnight at 10-20° C. below the melting temperature (Tm) of the hybrid in 6×SSPE, 5×Denhardt's solution, 0.1% SDS, 0.1 mg/ml denatured DNA. Tm for oligonucleotide probes can be determined by the following formula:

$$Tm(° C.) = 2(\text{number } T/A \text{ base pairs}) + 4(\text{number } G/C \text{ base pairs})$$

(Suggs et al., 1981).

Washes can typically be out as follows:
(1) Twice at room temperature for 15 minutes 1×SSPE, 0.1% SDS (low stringency wash).
(2) Once at the hybridization temperature for 15 minutes in 1×SSPE, 0.1% SDS (moderate stringency wash).

In general, salt and/or temperature can be altered to change stringency. With a labeled DNA fragment >70 or so bases in length, the following conditions can be used:

TABLE 1

| | |
|---|---|
| Low: | 1 or 2x SSPE, room temperature |
| Low: | 1 or 2x SSPE, 42° C. |
| Moderate: | 0.2x or 1x SSPE, 65° C. |
| High: | 0.1x SSPE, 65° C. |

Duplex formation and stability depend on substantial complementarity between the two strands of a hybrid, and, as noted above, a certain degree of mismatch can be tolerated. Therefore, the probe sequences of the subject invention include mutations (both single and multiple), deletions, insertions of the described sequences, and combinations thereof, wherein said mutations, insertions and deletions permit formation of stable hybrids with the target polynucleotide of interest. Mutations, insertions, and deletions can be produced in a given polynucleotide sequence in many ways, and these methods are known to an ordinarily skilled artisan. Other methods may become known in the future.

PCR Technology.

Polymerase Chain Reaction (PCR) is a repetitive, enzymatic, primed synthesis of a nucleic acid sequence. This procedure is well known and commonly used by those skilled in this art (see Mullis, U.S. Pat. Nos. 4,683,195, 4,683,202, and 4,800,159; Saiki et al., 1985). PCR is based on the enzymatic amplification of a DNA fragment of interest that is flanked by two oligonucleotide primers that hybridize to opposite strands of the target sequence. The primers are preferably oriented with the 3' ends pointing towards each other. Repeated cycles of heat denaturation of the template, annealing of the primers to their complementary sequences, and extension of the annealed primers with a DNA polymerase result in the amplification of the segment defined by the 5' ends of the PCR primers. The extension product of each primer can serve as a template for the other primer, so each cycle essentially doubles the amount of DNA fragment produced in the previous cycle. This results in the exponential accumulation of the specific target fragment, up to several million-fold in a few hours. By using a thermostable DNA polymerase such as Taq polymerase, isolated from the thermophilic bacterium *Thermus aquaticus*, the amplification process can be completely automated. Other enzymes which can be used are known to those skilled in the art.

Exemplified DNA sequences, or segments thereof, can be used as primers for PCR amplification. In performing PCR amplification, a certain degree of mismatch can be tolerated between primer and template. Therefore, mutations, deletions, and insertions (especially additions of nucleotides to the 5' end) of the exemplified primers fall within the scope of the subject invention. Mutations, insertions, and deletions can be produced in a given primer by methods known to an ordinarily skilled artisan.

Modification of Genes and Proteins.

The subject genes and proteins can be fused to other genes and proteins to produce chimeric or fusion proteins. The genes and proteins useful according to the subject invention include not only the specifically exemplified full-length sequences, but also portions, segments and/or fragments (including contiguous fragments and internal and/or terminal deletions compared to the full-length molecules) of these sequences, variants, mutants, chimerics, and fusions thereof. Proteins of the subject invention can have substituted amino acids so long as they retain desired functional activity. "Variant" genes have nucleotide sequences that encode the same proteins or equivalent proteins having activity equivalent or similar to an exemplified protein. The terms "variant proteins" and "equivalent proteins" refer to proteins having the same or essentially the same biological/functional activity against the target substrates and equivalent sequences as the exemplified proteins. As used herein, reference to an "equivalent" sequence refers to sequences having amino acid substitutions, deletions, additions, or insertions that improve or do not adversely affect activity to a significant extent. Fragments retaining activity are also included in this definition. Fragments and other equivalents that retain the same or similar function or activity as a corresponding fragment of an exemplified protein are within the scope of the subject invention. Changes, such as amino acid substitutions or additions, can be made for a variety of purposes, such as increasing (or decreasing) protease stability of the protein (without materially/substantially decreasing the functional activity of the protein), removing or adding a restriction site, and the like. Variations of genes may be readily constructed using standard techniques for making point mutations, for example.

In addition, U.S. Pat. No. 5,605,793, for example, describes methods for generating additional molecular diversity by using DNA reassembly after random or focused fragmentation. This can be referred to as gene "shuffling," which typically involves mixing fragments (of a desired size) of two or more different DNA molecules, followed by repeated rounds of renaturation. This can improve the activity of a protein encoded by a starting gene. The result is a chimeric protein having improved activity, altered substrate specificity, increased enzyme stability, altered stereospecificity, or other characteristics.

"Shuffling" can be designed and targeted after obtaining and examining the atomic 3D (three dimensional) coordinates and crystal structure of a protein of interest. Thus, "focused shuffling" can be directed to certain segments of a protein that are ideal for modification, such as surface-exposed segments, and preferably not internal segments that are involved with protein folding and essential 3D structural integrity.

Variant genes can be used to produce variant proteins; recombinant hosts can be used to produce the variant proteins. Using "gene shuffling" and other techniques, equivalent genes and proteins can be constructed that comprise certain segments having certain contiguous residues (amino acid or nucleotide) of any sequence exemplified herein. Such techniques can be adjusted to obtain equivalent/functionally active proteins having, for example, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, and 170 contiguous amino acid residues corresponding to a segment (of the same size) in any of the exemplified or suggested sequences. Polynucleotides encoding such segments, particularly for regions of interest, are also included in the subject invention and can also be used as probes and/or primers, especially for conserved regions.

Fragments of full-length genes can be made using commercially available exonucleases or endonucleases according to standard procedures. For example, enzymes such as Bal31 or site-directed mutagenesis can be used to systematically cut off nucleotides from the ends of these genes. Also, genes that encode active fragments may be obtained using a variety of restriction enzymes. Proteases may be used to directly obtain active fragments of these proteins.

It is within the scope of the invention as disclosed herein that proteins can be truncated and still retain functional activity. By "truncated protein" it is meant that a portion of a protein may be cleaved off while the remaining truncated protein retains and exhibits the desired activity after cleavage. Cleavage can be achieved by various proteases. Furthermore, effectively cleaved proteins can be produced using molecular biology techniques wherein the DNA bases encoding said protein are removed either through digestion with restriction endonucleases or other techniques available to the skilled artisan. After truncation, said proteins can be expressed in heterologous systems such as E. coli, baculoviruses, plant-based viral systems, yeast, and the like and then placed in insect assays as disclosed herein to determine activity. It is well-known in the art that truncated proteins can be successfully produced so that they retain functional activity while having less than the entire, full-length sequence. For example, B.t. proteins can be used in a truncated (core protein) form (see, e.g., Höfte et al. (1989), and Adang et al. (1985)). As used herein, the term "protein" can include functionally active truncations.

In some cases, especially for expression in plants, it can be advantageous to use truncated genes that express truncated proteins. Preferred truncated genes will typically encode 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, or 99% of the full-length protein.

Certain proteins of the subject invention have been specifically exemplified herein. As these proteins are merely exemplary of the proteins of the subject invention, it should be readily apparent that the subject invention comprises variant or equivalent proteins (and nucleotide sequences coding for equivalents thereof) having the same or similar activity of the exemplified proteins. Equivalent proteins will have amino acid similarity (and/or homology) with an exemplified protein. The amino acid identity will typically be at least 60%, preferably at least 75%, more preferably at least 80%, even more preferably at least 90%, and can be at least 95%. Preferred proteins of the subject invention can also be defined in terms of more particular identity and/or similarity ranges. For example, the identity and/or similarity can be 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, or 99% as compared to a sequence exemplified or suggested herein. Any number listed above can be used to define the upper and lower limits.

Unless otherwise specified, as used herein, percent sequence identity and/or similarity of two nucleic acids is determined using the algorithm of Karlin and Altschul, 1990, modified as in Karlin and Altschul 1993. Such an algorithm is incorporated into the NBLAST and XBLAST programs of Altschul et al., 1990. BLAST nucleotide searches are performed with the NBLAST program, score=100, wordlength=12. Gapped BLAST can be used as described in Altschul et al., 1997. When utilizing BLAST and Gapped BLAST programs, the default parameters of the respective programs (NBLAST and XBLAST) are used. See NCBI/NIH website. To obtain gapped alignments for comparison purposes, the AlignX function of Vector NTI Suite 8 (InforMax, Inc., North Bethesda, Md., U.S.A.), was used employing the default parameters. These were: a Gap opening penalty of 15, a Gap extension penalty of 6.66, and a Gap separation penalty range of 8.

Various properties and three-dimensional features of the protein can also be changed without adversely affecting the activity/functionality of the protein. Conservative amino acid substitutions can be tolerated/made to not adversely affect the activity and/or three-dimensional configuration of the molecule. Amino acids can be placed in the following classes: non-polar, uncharged polar, basic, and acidic. Conservative substitutions whereby an amino acid of one class is replaced with another amino acid of the same type fall within the scope of the subject invention so long as the substitution is not adverse to the biological activity of the compound. Table 2 provides a listing of examples of amino acids belonging to each class.

TABLE 2

| Class of Amino Acid | Examples of Amino Acids |
| --- | --- |
| Nonpolar | Ala, Val, Leu, Ile, Pro, Met, Phe, Trp |
| Uncharged Polar | Gly, Ser, Thr, Cys, Tyr, Asn, Gln |
| Acidic | Asp, Glu |
| Basic | Lys, Arg, His |

In some instances, non-conservative substitutions can also be made. However, preferred substitutions do not significantly detract from the functional/biological activity of the protein.

As used herein, reference to "isolated" polynucleotides and/or "purified" proteins refers to these molecules when they are in a state other than which they would be found in nature. Thus, reference to "isolated" and/or "purified" signifies the involvement of the "hand of man" as described herein. For example, a bacterial "gene" of the subject invention put into a plant for expression is an "isolated polynucleotide." Likewise, a protein derived from a bacterial protein and produced by a plant is an "isolated protein."

Because of the degeneracy/redundancy of the genetic code, a variety of different DNA sequences can encode the amino acid sequences disclosed herein. It is well within the skill of a person trained in the art to create alternative DNA sequences that encode the same, or essentially the same, proteins. These variant DNA sequences are within the scope of the subject invention. This is also discussed in more detail below in the section entitled "Optimization of sequence for expression in plants."

Optimization of Sequence for Expression in Plants.

To obtain high expression of heterologous genes in plants it is generally preferred to reengineer the genes so that they are more efficiently expressed in (the cytoplasm of) plant cells. Maize is one such plant where it may be preferred to re-design the heterologous gene(s) prior to transformation to increase the expression level thereof in said plant. Therefore, an additional step in the design of genes encoding a bacterial protein is reengineering of a heterologous gene for optimal expression, using codon bias more closely aligned with the target plant sequence, whether a dicot or monocot species. Sequences can also be optimized for expression in any of the more particular types of plants discussed elsewhere herein.

Transgenic Hosts.

The protein-encoding genes of the subject invention can be introduced into a wide variety of microbial or plant hosts. The subject invention includes transgenic plant cells and transgenic plants. Preferred plants (and plant cells) are corn, *Arabidopsis*, tobacco, soybeans, cotton, canola, rice, wheat, turf and pasture grasses, and the like. Other types of transgenic plants can also be made according to the subject invention, such as fruits, vegetables, ornamental plants, and trees. More generally, dicots and/or monocots can be used in various aspects of the subject invention.

Thus, the subject invention can be adapted for use with vascular and nonvascular plants including monocots and dicots, conifers, bryophytes, algae, fungi, and bacteria. Animal cells and animal cell cultures are also a possibility.

In preferred embodiments, expression of the gene results, directly or indirectly, in the intracellular production (and maintenance) of the protein(s) of interest. Plants can be rendered herbicide-resistant in this manner. Such hosts can be referred to as transgenic, recombinant, transformed, and/or transfected hosts and/or cells. In some aspects of this invention (when cloning and preparing the gene of interest, for example), microbial (preferably bacterial) cells can be produced and used according to standard techniques, with the benefit of the subject disclosure.

Plant cells transfected with a polynucleotide of the subject invention can be regenerated into whole plants. The subject invention includes cell cultures including tissue cell cultures, liquid cultures, and plated cultures. Seeds produced by and/or used to generate plants of the subject invention are also included within the scope of the subject invention. Other plant tissues and parts are also included in the subject invention. The subject invention likewise includes methods of producing plants or cells comprising a polynucleotide of the subject invention. One preferred method of producing such plants is by planting a seed of the subject invention.

Insertion of Genes to Form Transgenic Hosts.

One aspect of the subject invention is the transformation/transfection of plants, plant cells, and other host cells with polynucleotides of the subject invention that express proteins of the subject invention. Plants transformed in this manner can be rendered resistant to a variety of herbicides with different modes of action.

A wide variety of methods are available for introducing a gene encoding a desired protein into the target host under conditions that allow for stable maintenance and expression of the gene. These methods are well known to those skilled in the art and are described, for example, in U.S. Pat. No. 5,135,867.

Vectors comprising a DSM-2 polynucleotide are included in the scope of the subject invention. For example, a large number of cloning vectors comprising a replication system in *E. coli* and a marker that permits selection of the transformed cells are available for preparation for the insertion of foreign genes into higher plants. The vectors comprise, for example, pBR322, pUC series, M13mp series, pACYC184, etc. Accordingly, the sequence encoding the protein can be inserted into the vector at a suitable restriction site. The resulting plasmid is used for transformation into *E. coli*. The *E. coli* cells are cultivated in a suitable nutrient medium, then harvested and lysed. The plasmid is recovered by purification away from genomic DNA. Sequence analysis, restriction analysis, electrophoresis, and other biochemical-molecular biological methods are generally carried out as methods of analysis. After each manipulation, the DNA sequence used can be restriction digested and joined to the next DNA sequence. Each plasmid sequence can be cloned in the same or other plasmids. Depending on the method of inserting desired genes into the plant, other DNA sequences may be necessary. If, for example, the Ti or Ri plasmid is used for the transformation of the plant cell, then at least the right border, but often the right and the left border of the Ti or Ri plasmid T-DNA, has to be joined as the flanking region of the genes to be inserted. The use of T-DNA for the transformation of plant cells has been intensively researched and described in EP 120 516; Hoekema (1985); Fraley et al. (1986); and An et al. (1985).

A large number of techniques are available for inserting DNA into a plant host cell. Those techniques include transformation with T-DNA using *Agrobacterium tumefaciens* or *Agrobacterium rhizogenes* as transformation agent, fusion, injection, biolistics (microparticle bombardment), silicon carbide whiskers, aerosol beaming, PEG, or electroporation as well as other possible methods. If *Agrobacteria* are used for the transformation, the DNA to be inserted has to be cloned into special plasmids, namely either into an intermediate vector or into a binary vector. The intermediate vectors can be integrated into the Ti or Ri plasmid by homologous recombination owing to sequences that are homologous to sequences in the T-DNA. The Ti or Ri plasmid also comprises the vir region necessary for the transfer of the T-DNA. Intermediate vectors cannot replicate themselves in *Agrobacteria*. The intermediate vector can be transferred into *Agrobacterium tumefaciens* by means of a helper plasmid (conjugation). Binary vectors can replicate themselves both in *E. coli* and in *Agrobacteria*. They comprise a selection marker gene and a linker or polylinker which are framed by the right and left T-DNA border regions. They can be transformed directly into *Agrobacteria* (Holsters, 1978). The *Agrobacterium* used as host cell is to comprise a plasmid carrying a vir region. The vir region is necessary for the transfer of the T-DNA into the plant cell. Additional T-DNA may be contained. The bacterium so transformed is used for the transformation of plant cells. Plant explants can be cultivated advantageously with *Agrobacterium turnefaciens* or *Agrobacterium rhizogenes* for the transfer of the DNA into the plant cell. Whole plants can then be regenerated from the infected plant material (for example, pieces of leaf, segments of stalk, roots, but also protoplasts or suspension-cultivated cells) in a suitable medium, which may contain antibiotics or biocides for selection. The plants so obtained can then be tested for the presence of the inserted DNA. No special demands are made of the plasmids in the case of injection and electroporation. It is possible to use ordinary plasmids, such as, for example, pUC derivatives.

The transformed cells grow inside the plants in the usual manner. They can form germ cells and transmit the transformed trait(s) to progeny plants. Such plants can be grown in the normal manner and crossed with plants that have the same transformed hereditary factors or other hereditary factors. The resulting hybrid individuals have the corresponding phenotypic properties.

In some preferred embodiments of the invention, genes encoding the bacterial protein are expressed from transcriptional units inserted into the plant genome. Preferably, said transcriptional units are recombinant vectors capable of stable integration into the plant genome and enable selection of transformed plant lines expressing mRNA encoding the proteins.

Once the inserted DNA has been integrated in the genome, it is relatively stable there (and does not come out again). It normally contains a selection marker that confers on the transformed plant cells resistance to a biocide or an antibiotic, such as kanamycin, G418, bleomycin, hygromycin, or chloramphenicol, inter alia. Plant selectable markers also typically can provide resistance to various herbicides such as glufosinate, (PAT), glyphosate (EPSPS), imazethyapyr (AHAS), and many others. The individually employed marker should accordingly permit the selection of transformed cells rather than cells that do not contain the inserted DNA. The gene(s) of interest are preferably expressed either by constitutive or inducible promoters in the plant cell. Once expressed, the mRNA is translated into proteins, thereby incorporating amino acids of interest into protein. The genes encoding a protein expressed in the plant cells can be under the control of a constitutive promoter, a tissue-specific promoter, or an inducible promoter.

Several techniques exist for introducing foreign recombinant vectors into plant cells, and for obtaining plants that stably maintain and express the introduced gene. Such techniques include the introduction of genetic material coated onto microparticles directly into cells (U.S. Pat. No. 4,945,050 to Cornell and U.S. Pat. No. 5,141,131 to Dow-Elanco, now Dow AgroSciences, LLC). In addition, plants may be transformed using *Agrobacterium* technology, see U.S. Pat. No. 5,177,010 to University of Toledo; U.S. Pat. No. 5,104,310 to Texas A&M; European Patent Application 0131624B1; European Patent Applications 120516, 159418B1 and 176,112 to Schilperoot; U.S. Pat. Nos. 5,149, 645, 5,469,976, 5,464,763 and 4,940,838 and 4,693,976 to Schilperoot; European Patent Applications 116718, 290799, 320500, all to Max Planck; European Patent Applications 604662 and 627752, and U.S. Pat. No. 5,591,616, to Japan Tobacco; European Patent Applications 0267159 and 0292435, and U.S. Pat. No. 5,231,019, all to Ciba Geigy, now Syngenta; U.S. Pat. Nos. 5,463,174 and 4,762,785, both to Calgene; and U.S. Pat. Nos. 5,004,863 and 5,159,135, both to Agracetus. Other transformation technology includes whiskers technology. See U.S. Pat. Nos. 5,302,523 and 5,464,765, both to Zeneca, now Syngenta Other direct DNA delivery transformation technology includes aerosol beam technology. See U.S. Pat. No. 6,809,232. Electroporation technology has also been used to transform plants. See WO 87/06614 to Boyce Thompson Institute; U.S. Pat. Nos. 5,472,869 and 5,384,253, both to Dekalb; and WO 92/09696 and WO 93/21335, both to Plant Genetic Systems. Furthermore, viral vectors can also be used to produce transgenic plants expressing the protein of interest. For example, monocotyledonous plants can be transformed with a viral vector using the methods described in U.S. Pat. No. 5,569,597 to Mycogen Plant Science and Ciba-Geigy (now Syngenta), as well as U.S. Pat. Nos. 5,589,367 and 5,316,931, both to Biosource, now Large Scale Biology.

As mentioned previously, the manner in which the DNA construct is introduced into the plant host is not critical to this invention. Any method that provides for efficient transformation may be employed. For example, various methods for plant cell transformation are described herein and include the use of Ti or Ri-plasmids and the like to perform *Agrobacterium* mediated transformation. In many instances, it will be desirable to have the construct used for transformation bordered on one or both sides by T-DNA borders, more specifically the right border. This is particularly useful when the construct uses *Agrobacterium tumefaciens* or *Agrobacterium rhizogenes* as a mode for transformation, although T-DNA borders may find use with other modes of transformation. Where *Agrobacterium* is used for plant cell transformation, a vector may be used which may be introduced into the host for homologous recombination with T-DNA or the Ti or Ri plasmid present in the host. Introduction of the vector may be performed via electroporation, tri-parental mating and other techniques for transforming gram-negative bacteria which are known to those skilled in the art. The manner of vector transformation into the *Agrobacterium* host is not critical to this invention. The Ti or Ri plasmid containing the T-DNA for recombination may be capable or incapable of causing gall formation, and is not critical to said invention so long as the vir genes are present in said host.

In some cases where *Agrobacterium* is used for transformation, the expression construct being within the T-DNA borders will be inserted into a broad spectrum vector such as pRK2 or derivatives thereof as described in Dina et al. (1980) and EPO 0 120 515. Included within the expression construct and the T-DNA will be one or more markers as described herein which allow for selection of transformed *Agrobacterium* and transformed plant cells. The particular marker employed is not essential to this invention, with the preferred marker depending on the host and construction used.

For transformation of plant cells using *Agrobacterium*, explants may be combined and incubated with the transformed *Agrobacterium* for sufficient time to allow transformation thereof. After transformation, the *Agrobacteria* are killed by selection with the appropriate antibiotic and plant cells are cultured with the appropriate selective medium. Once calli are formed, shoot formation can be encouraged by employing the appropriate plant hormones according to methods well known in the art of plant tissue culturing and plant regeneration. However, a callus intermediate stage is not always necessary. After shoot formation, said plant cells can be transferred to medium which encourages root formation thereby completing plant regeneration. The plants may then be grown to seed and said seed can be used to establish future generations. Regardless of transformation technique, the gene encoding a bacterial protein is preferably incorporated into a gene transfer vector adapted to express said gene in a plant cell by including in the vector a plant promoter regulatory element, as well as 3' non-translated transcriptional termination regions such as Nos and the like.

In addition to numerous technologies for transforming plants, the type of tissue that is contacted with the foreign genes may vary as well. Such tissue would include but would not be limited to embryogenic tissue, callus tissue types I, II, and III, hypocotyl, meristem, root tissue, tissues for expression in phloem, and the like. Almost all plant tissues may be transformed during dedifferentiation using appropriate techniques described herein.

In addition to a selectable marker, it may be desirous to use a reporter gene. In some instances a reporter gene may be used with or without a selectable marker. Reporter genes are genes that are typically not present in the recipient organism or tissue and typically encode for proteins resulting in some phenotypic change or enzymatic property. Examples of such genes are provided in Weising et al., 1988. Preferred reporter genes include the beta-glucuronidase (GUS) of the uidA locus of E. coli, the chloramphenicol acetyl transferase gene from Tn9 of E. coli, the green fluorescent protein from the bioluminescent jellyfish Aequorea victoria, and the luciferase genes from firefly Photinus pyralis. An assay for detecting reporter gene expression may then be performed at a suitable time after said gene has been introduced into recipient cells. A preferred such assay entails the use of the gene encoding beta-glucuronidase (GUS) of the uidA locus of E. coli as described by Jefferson et al., (1987) to identify transformed cells.

In addition to plant promoter regulatory elements, promoter regulatory elements from a variety of sources can be used efficiently in plant cells to express foreign genes. For example, promoter regulatory elements of bacterial origin, such as the octopine synthase promoter, the nopaline synthase promoter, the mannopine synthase promoter; promoters of viral origin, such as the cauliflower mosaic virus (35S and 19S), 35T (which is a re-engineered 35S promoter, see U.S. Pat. No. 6,166,302, especially Example 7E) and the like may be used. Plant promoter regulatory elements include but are not limited to ribulose-1,6-bisphosphate (RUBP) carboxylase small subunit (ssu), beta-conglycinin promoter, beta-phaseolin promoter, ADH promoter, heat-shock promoters, and tissue specific promoters. Other elements such as matrix attachment regions, scaffold attachment regions, introns, enhancers, polyadenylation sequences and the like may be present and thus may improve the transcription efficiency or DNA integration. Such elements may or may not be necessary for DNA function, although they can provide better expression or functioning of the DNA by affecting transcription, mRNA stability, and the like. Such elements may be included in the DNA as desired to obtain optimal performance of the transformed DNA in the plant. Typical elements include but are not limited to Adh-intron 1, Adh-intron 6, the alfalfa mosaic virus coat protein leader sequence, osmotin UTR sequences, the maize streak virus coat protein leader sequence, as well as others available to a skilled artisan. Constitutive promoter regulatory elements may also be used thereby directing continuous gene expression in all cells types and at all times (e.g., actin, ubiquitin, CaMV 35S, and the like). Tissue specific promoter regulatory elements are responsible for gene expression in specific cell or tissue types, such as the leaves or seeds (e.g., zein, oleosin, napin, ACP, globulin and the like) and these may also be used.

Promoter regulatory elements may also be active (or inactive) during a certain stage of the plant's development as well as active in plant tissues and organs. Examples of such include but are not limited to pollen-specific, embryo-specific, corn-silk-specific, cotton-fiber-specific, root-specific, seed-endosperm-specific, or vegetative phase-specific promoter regulatory elements and the like. Under certain circumstances it may be desirable to use an inducible promoter regulatory element, which is responsible for expression of genes in response to a specific signal, such as: physical stimulus (heat shock genes), light (RUBP carboxylase), hormone (Em), metabolites, chemical (tetracycline responsive), and stress. Other desirable transcription and translation elements that function in plants may be used. Numerous plant-specific gene transfer vectors are known in the art.

Plant RNA viral based systems can also be used to express bacterial protein. In so doing, the gene encoding a protein can be inserted into the coat promoter region of a suitable plant virus which will infect the host plant of interest. The protein can then be expressed thus providing protection of the plant from herbicide damage. Plant RNA viral based systems are described in U.S. Pat. No. 5,500,360 to Mycogen Plant Sciences, Inc. and U.S. Pat. Nos. 5,316,931 and 5,589,367 to Biosource, now Large Scale Biology.

Selection Agents.

In addition to glufosinate and bialaphos, selection agents that can be used according to the subject invention include all synthetic and natural analogs that may be inactivitated by the acetyl transferase mechanism mediated by a DSM-2 gene of the subject invention. See e.g. FIG. 1.

Unless specifically indicated or implied, the terms "a", "an", and "the" signify "at least one" as used herein.

All patents, patent applications, provisional applications, and publications referred to or cited herein are incorporated by reference in their entirety to the extent they are not inconsistent with the explicit teachings of this specification.

Following are examples that illustrate procedures for practicing the invention. These examples should not be construed as limiting. All percentages are by weight and all solvent mixture proportions are by volume unless otherwise noted.

Example 1—Method for Identifying Genes that Impart Resistance to Glufosinate in Planta As a way to identify genes which possess herbicide degrading activities in planta, or cell culture, it is possible to mine current public databases such as NCBI (National Center for Biotechnology Information). To begin the process, it is necessary to have a functional gene sequence already identified that encodes a protein with the desired characteristics (i.e., phosphinothricin acetyltransferase). This protein sequence is then used as the input for the BLAST (Basic Local Alignment Search Tool) (Altschul et al., 1997) algorithm to compare against available NCBI protein sequences deposited. Using default settings, this search returns upwards of 100 homologous protein sequences at varying levels. These range from highly identical (85-98%) to very low identity (23-32%) at the amino acid level. Traditionally only sequences with high homology would be expected to retain similar properties to the input sequence. In this case, only resulting sequences with ≤50% homology were chosen. As exemplified herein, cloning and recombinantly expressing homologues with as little as 30% amino acid conservation (relative to pat from Streptomyces hygroscopicus) can be used to select transformed plant cell cultures from untransformed.

DSM-2 was identified from the NCBI database (see the ncbi.nlm.nih.gov website; accession # AAA26705) as a homologue with only 30% amino acid identity to pat and 28% to bar. Percent identity was determined by first translating the nucleotide sequences deposited in the database to proteins, then using ClustalW in the VectorNTI software package to perform the multiple sequence alignment.

Example 2—Optimization of Sequence for Expression in Plants and Bacteria 2.1—Background.

To obtain higher levels of expression of heterologous genes in plants, it may be preferred to reengineer the protein encoding sequence of the genes so that they are more efficiently expressed in plant cells. Maize is one such plant where it may be preferred to re-design the heterologous protein coding region prior to transformation to increase the expression level of the gene and the level of encoded protein in the plant. Therefore, an additional step in the design of genes encoding a bacterial protein is reengineering of a heterologous gene for optimal expression. See e.g. Kawabe et al. (2003), "Patterns of Codon Usage Bias in Three Dicot and Four Monocot Plant Species," Genes Genet. Syst., pp. 343-352; and Ikemura et al. (1993), "Plant Molecular Biology Labfax", Croy, ed., Bios Scientific Publishers Ltd., p. 3748), and all relevant references cited therein.

One reason for the reengineering of a bacterial protein for expression in maize, for example, is due to the non-optimal G+C content of the native gene. For example, the very low G+C content of many native bacterial gene(s) (and consequent skewing towards high A+T content) results in the generation of sequences mimicking or duplicating plant gene control sequences that are known to be highly A+T rich. The presence of some A+T-rich sequences within the DNA of gene(s) introduced into plants (e.g., TATA box regions normally found in gene promoters) may result in aberrant transcription of the gene(s). On the other hand, the presence of other regulatory sequences residing in the transcribed mRNA (e.g., polyadenylation signal sequences (AAUAAA), or sequences complementary to small nuclear RNAs involved in pre-mRNA splicing) may lead to RNA instability. Therefore, one goal in the design of genes encoding a bacterial protein for maize expression, more preferably referred to as plant optimized gene(s), is to generate a DNA sequence having a higher G+C content, and preferably one close to that of maize genes coding for metabolic enzymes. Another goal in the design of the plant optimized gene(s) encoding a bacterial protein is to generate a DNA sequence in which the sequence modifications do not hinder translation.

Table 3 illustrates how high the G+C content is in maize. For the data in Table 3, coding regions of the genes were extracted from GenBank (Release 71) entries, and base compositions were calculated using the MacVector™ program (Accelerys, San Diego, Calif.). Intron sequences were ignored in the calculations.

Due to the plasticity afforded by the redundancy/degeneracy of the genetic code (i.e., some amino acids are specified by more than one codon), evolution of the genomes in different organisms or classes of organisms has resulted in differential usage of redundant codons. This "codon bias" is reflected in the mean base composition of protein coding regions. For example, organisms with relatively low G+C contents utilize codons having A or T in the third position of redundant codons, whereas those having higher G+C contents utilize codons having G or C in the third position. It is thought that the presence of "minor" codons within an mRNA may reduce the absolute translation rate of that mRNA, especially when the relative abundance of the charged tRNA corresponding to the minor codon is low. An extension of this is that the diminution of translation rate by individual minor codons would be at least additive for multiple minor codons. Therefore, mRNAs having high relative contents of minor codons would have correspondingly low translation rates. This rate would be reflected by subsequent low levels of the encoded protein.

In engineering genes encoding a bacterial protein for expression in maize (corn, or other plants, such as cotton, soybeans, wheat, Brassica/canola, rice; or more generally for oil crops, monocots, dicots, and hemicot/plants in general), the codon bias of the plant has been determined. The codon bias for maize is the statistical codon distribution that the plant uses for coding its proteins and the preferred codon usage is shown in Table 4. After determining the bias, the percent frequency of the codons in the gene(s) of interest is determined. The primary codons preferred by the plant should be determined, as well as the second, third, and fourth choices of preferred codons when multiple choices exist. A new DNA sequence can then be designed which encodes the amino sequence of the bacterial protein, but the new DNA sequence differs from the native bacterial DNA sequence (encoding the protein) by the substitution of the plant (first preferred, second preferred, third preferred, or fourth preferred) codons to specify the amino acid at each position within the protein amino acid sequence. The new sequence is then analyzed for restriction enzyme sites that might have been created by the modification. The identified sites are further modified by replacing the codons with first, second, third, or fourth choice preferred codons. Other sites in the sequence which could affect transcription or translation of the gene of interest are the exon:intron junctions (5' or 3'), poly A addition signals, or RNA polymerase termination signals. The sequence is further analyzed and modified to reduce the frequency of TA or GC doublets. In addition to the doublets, G or C sequence blocks that have more than about four residues that are the same can affect transcription of the sequence. Therefore, these blocks are also modified by replacing the codons of first or second choice, etc. with the next preferred codon of choice.

TABLE 3

Compilation of G + C contents of protein coding regions of maize genes

| Protein Class[a] | Range % G + C | Mean % G + C[b] |
| --- | --- | --- |
| Metabolic Enzymes (76) | 44.4-75.3 | 59.0 (.+−.8.0) |
| Structural Proteins (18) | 48.6-70.5 | 63.6 (.+−.6.7) |
| Regulatory Proteins (5) | 57.2-68.8 | 62.0 (.+−.4.9) |
| Uncharacterized Proteins (9) | 41.5-70.3 | 64.3 (.+−.7.2) |
| All Proteins (108) | 44.4-75.3 | 60.8 (.+−.5.2)[c] |

[a]Number of genes in class given in parentheses.
[b]Standard deviations given in parentheses.
[c]Combined groups mean ignored in mean calculation

TABLE 4

Preferred amino acid codons for proteins expressed in maize

| Amino Acid | Codon* |
| --- | --- |
| Alanine | GCC/GCG |
| Cysteine | TGC/TGT |
| Aspartic Acid | GAC/GAT |
| Glutamic Acid | GAG/GAA |

TABLE 4-continued

Preferred amino acid codons for proteins expressed in maize

| Amino Acid | Codon* |
|---|---|
| Phenylalanine | TTC/TTT |
| Glycine | GGC/GGG |
| Histidine | CAC/CAT |
| Isoleucine | ATC/ATT |
| Lysine | AAG/AAA |
| Leucine | CTG/CTC |
| Methionine | ATG |
| Asparagine | AAC/AAT |
| Proline | CCG/CCA |
| Glutamine | CAG/CAA |
| Arginine | AGG/CGC |
| Serine | AGC/TCC |
| Threonine | ACC/ACG |
| Valine | GTG/GTC |
| Tryptophan | TGG |
| Tryrosine | TAC/TAT |
| Stop | TGA/TAG |

It is preferred that the plant optimized gene(s) encoding a bacterial protein contain about 63% of first choice codons, between about 22% to about 37% second choice codons, and between about 15% to about 0% third or fourth choice codons, wherein the total percentage is 100%. Most preferred the plant optimized gene(s) contains about 63% of first choice codons, at least about 22% second choice codons, about 7.5% third choice codons, and about 7.5% fourth choice codons, wherein the total percentage is 100%. The method described above enables one skilled in the art to modify gene(s) that are foreign to a particular plant so that the genes are optimally expressed in plants. The method is further illustrated in PCT application WO 97/13402.

Thus, in order to design plant optimized genes encoding a bacterial protein, a DNA sequence is designed to encode the amino acid sequence of said protein utilizing a redundant genetic code established from a codon bias table compiled from the gene sequences for the particular plant or plants. The resulting DNA sequence has a higher degree of codon diversity, a desirable base composition, can contain strategically placed restriction enzyme recognition sites, and lacks sequences that might interfere with transcription of the gene, or translation of the product mRNA. Thus, synthetic genes that are functionally equivalent to the proteins/genes of the subject invention can be used to transform hosts, including plants. Additional guidance regarding the production of synthetic genes can be found in, for example, U.S. Pat. No. 5,380,831.

2.2—DSM-2 Plant Rebuild Analysis.

Extensive analysis of the 513 base pairs (bp) of the DNA sequence of the native DSM-2 coding region (SEQ ID NO:1) revealed the presence of several sequence motifs that are thought to be detrimental to optimal plant expression, as well as a non-optimal codon composition. The protein encoded by SEQ ID NO:1 is presented as SEQ ID NO:2. To improve production of the recombinant protein in monocots as well as dicots, a "plant-optimized" DNA sequence DSM-2 v2 (SEQ ID NO:3) was developed that encodes a protein which is identical to the native sequence disclosed as SEQ ID NO:2. In contrast, the native and plant-optimized DNA sequences of the coding regions are only 78.3% identical. Table 5 shows the differences in codon compositions of the native (Columns A and D) and plant-optimized sequences (Columns B and E), and allows comparison to a theoretical plant-optimized sequence (Columns C and F).

TABLE 5

Codon composition comparisons of coding regions of Native DSM-2, Plant-Optimized version (v2) and a Theoretical Plant-Optimized version.

| Amino Acid | Codon | A Native # | B Plant Opt v2 # | C Theor. Plant Opt. # | Amino Acid | Codon | D Native # | E Plant Opt v2 # | F Theor. Plant Opt. # |
|---|---|---|---|---|---|---|---|---|---|
| ALA (A) | GCA | 0 | 5 | 5 | LEU (L) | CTA | 0 | 0 | 0 |
|  | GCC | 14 | 7 | 7 |  | CTC | 8 | 5 | 5 |
|  | GCG | 6 | 0 | 0 |  | CTG | 6 | 0 | 0 |
|  | GCT | 0 | 8 | 8 |  | CTT | 0 | 5 | 5 |
| ARG (R) | AGA | 2 | 4 | 4 |  | TTA | 0 | 0 | 0 |
|  | AGG | 1 | 5 | 5 |  | TTG | 0 | 4 | 4 |
|  | CGA | 1 | 0 | 0 | LYS (K) | AAA | 0 | 1 | 1 |
|  | CGC | 8 | 3 | 3 |  | AAG | 3 | 2 | 2 |
|  | CGG | 3 | 0 | 0 | MET (M) | ATG | 1 | 1 | 1 |
|  | CGT | 1 | 4 | 4 | PHE (F) | TTC | 6 | 2 | 4 |
| ASN (N) | AAC | 2 | 1 | 1 |  | TTT | 0 | 4 | 2 |
|  | AAT | 0 | 1 | 1 | PRO (P) | CCA | 1 | 6 | 6 |
| ASP (D) | GAC | 7 | 4 | 4 |  | CCC | 4 | 3 | 3 |
|  | GAT | 1 | 4 | 4 |  | CCG | 8 | 0 | 0 |
| CYS (C) | TGC | 0 | 0 | 0 |  | CCT | 1 | 5 | 5 |
|  | TGT | 0 | 0 | 0 | SER (S) | AGC | 1 | 2 | 2 |
| END | TAA | 0 | 0 | 0 |  | AGT | 0 | 0 | 0 |
|  | TAG | 1 | 0 | 0 |  | TCA | 1 | 2 | 2 |
|  | TGA | 0 | 1 | 1 |  | TCC | 4 | 2 | 2 |
| GLN (Q) | CAA | 0 | 2 | 1 |  | TCG | 2 | 0 | 0 |
|  | CAG | 3 | 1 | 2 |  | TCT | 0 | 2 | 2 |

TABLE 5-continued

Codon composition comparisons of coding regions of Native DSM-2, Plant-Optimized version (v2) and a Theoretical Plant-Optimized version.

| Amino Acid | Codon | A Native # | B Plant Opt v2 # | C Theor. Plant Opt. # | Amino Acid | Codon | D Native # | E Plant Opt v2 # | F Theor. Plant Opt. # |
|---|---|---|---|---|---|---|---|---|---|
| GLU (E) | GAA | 1 | 6 | 6 | THR (T) | ACA | 1 | 2 | 3 |
|  | GAG | 14 | 9 | 9 |  | ACC | 5 | 5 | 5 |
| GLY (G) | GGA | 2 | 4 | 4 |  | ACG | 4 | 0 | 0 |
|  | GGC | 9 | 4 | 4 |  | ACT | 2 | 5 | 4 |
|  | GGG | 2 | 2 | 2 | TRP (W) | TGG | 3 | 3 | 3 |
|  | GGT | 1 | 4 | 4 | TYR (Y) | TAC | 12 | 7 | 8 |
| HIS (H) | CAC | 5 | 3 | 3 |  | TAT | 0 | 5 | 4 |
|  | CAT | 0 | 2 | 2 | VAL (V) | GTA | 1 | 0 | 0 |
| ILE (I) | ATA | 0 | 1 | 1 |  | CTC | 5 | 3 | 3 |
|  | ATC | 4 | 2 | 2 |  | GTG | 4 | 4 | 4 |
|  | ATT | 0 | 1 | 1 |  | GTT | 1 | 4 | 4 |
|  | Totals | 88 | 88 | 88 |  | Totals | 84 | 84 | 84 |

It is clear from examination of Table 5 that the native and plant-optimized coding regions, while encoding identical proteins, are substantially different from one another. The plant-optimized version (v1) closely mimics the codon composition of a theoretical plant-optimized coding region encoding the DSM-2 protein.

Example 3—Cloning of Transformation Vectors 3.1—Construction of Binary Plasmids Containing DSM-2 (v2)

The DSM-2 (v2) codon optimized gene coding sequence (DASPICO45) was cut with the restriction enzymes BbsI (New England Biolabs, Inc., Beverly Mass., cat # R0539s) and SacI (New England Biolabs, Inc., cat # R0156s). The resulting fragment was ligated into pDAB773 at the corresponding restriction sites, NcoI (New England Biolabs, cat # R0193s) and SacI. Positive colonies were identified via restriction enzyme digestion. The resulting clones contained the Rb7 MAR v3//At Ubi10 promoter v2//gene of interest//Atu Orf 1 3'UTR v3. The plasmid that contained DSM-2 (v2) as the gene of interest were labeled as pDAB3774.

The Rb7 MAR v3//AtUbi10 promoter v2//gene of interest//Atu Orf1 3'UTR v3 cassette was cloned into the binary vector pDAB3736 as an AgeI (New England Biolabs, Inc., cat # R0552s) restriction fragment. This cassette was cloned between the Left Hand and Right Hand Borders of the binary plasmid. Positive colonies were identified via restriction enzyme digestion and sequencing reactions. The constructs containing Rb7 MAR v3//AtUbi10 promoter v2//DSM-2 v2//Atu Orf1 3'UTR v3 were labeled as pDAB3778.

A control construct containing the Rb7 MAR v3//AtUbi10 promoter v2//PAT v3//Atu Orf1 3'UTR v3 cassette was completed by removing the GateWay attR destination cassette from pDAB3736. pDAB3736 was digested with the PacI (New England Biolabs, Inc., cat # R0547s) restriction enzyme. PacI flanks the GateWay attR destination cassette in pDAB3736. The PacI digested plasmid was self ligated and transformed into *Escherichia coli* Top10 cells (Invitrogen, Carlsbad Calif., cat # C4040-10). Positive colonies were identified via restriction enzyme digestion and sequencing reactions. The resulting construct was labeled as pDAB3779.

3.2—Cloning of Additional Transformation Constructs.

All other constructs created for transformation into appropriate plant species were built using similar procedures as previously described herein, and other standard molecular cloning methods (Maniatis et al., 1982). Table 6 lists all the transformation constructs used with appropriate promoters and features defined, as well as the crop transformed.

TABLE 6

Constructs used in transformation of various plant species.

| pDAB # | pDAS # | Species * Transformed into | Gene of interest (GOI) | Promoter | Feature 1 | Feature 2 | GOI 2 | Promoter | Bacterial Selection gene | Bacterial Selection gene 2 | Plant Selection gene | Promoter | Trxn Method |
|---|---|---|---|---|---|---|---|---|---|---|---|---|---|
| 3247 | | A | DSM2 (v2) | CsVMV | NtOsm | RB7 Mar v2 | — | — | Spectinomycin | — | AAD12 (v1) | AtUbi10 | Agra binary |
| 3250 | 1941 | R, Cn | DSM2 (v2) | ZmUbi1 | NtOsm | RB7 Mar v2 | — | — | Spectinomycin | — | — | — | Whiskers |
| 3251 | 1942 | R, Cn | PAT | ZmUbi1 | NtOsm | RB7 Mar v2 | — | — | Spectinomycin | — | — | — | Whiskers |
| 3778 | 1861 | T | DSM2 (v2) | AtUbi10 | — | RB7 Mar v2 | — | — | Spectinomycin | — | — | — | Agro binary |

TABLE 6-continued

Constructs used in transformation of various plant species.

| pDAB # | pDAS # | Species * Transformed into | Gene of interest (GOI) | Promoter | Feature 1 | Feature 2 | GOI 2 | Promoter | Bacterial Selection gene | Bacterial Selection gene 2 | Plant Selection gene | Promoter | Trxn Method |
|---|---|---|---|---|---|---|---|---|---|---|---|---|---|
| 3779 | 1862 | T | PAT | AtUbi10 | — | RB7 Mar v2 | — | — | Spectinomycin | — | — | — | Agro binary |

*A = *Arabidopsis*
T = Tobacco
R = Rice
Cn = Corn
CsVMV = Cassava Vein Mosaic Virus Promoter
AtUbi10 = *Arabidopsis thaliana* Ubiquitin 10 Promoter
RB7 Mar v2 = *Nicotiana tabacum* matrix associated region (MAR)
NtOsm = *Nicotiana tabacum* Osmotin 5' and 3' Untranslated Regions
ZmUbi1 = *Zea mays* Ubiquitin 1 Promoter Example 4—Complementation of Sensitive *E. Coli* (BL-21) with DSM-2 (V2) Using Prokaryotic and Euraryotic Promoters 4.1—Construction of *Escherichia coli* Expression Plasmid Containing DSM-2 (v2)

The DSM-2 (v2) codon optimized sequence was digested with the restriction enzymes BbsI and SacI. The resulting fragment was cloned into pDAB779 at the corresponding restriction sites of NcoI and SacI. pDAB779 is a pET28a(+) expression vector (Novagen, Madison Wis., cat #69864-3). Positive colonies containing the DSM-2 (v2) gene coding sequence were identified via restriction enzyme digestion. The DSM-2//pET28a(+) constructs were labeled as pDAB4412.

The expression plasmids pET (empty vector control), and pDAB4412 were transformed into the *E. coli* T7 expression strain BL21—Star (DE3) (Invitrogen, Carlsbad Calif., cat # C6010-03) using standard methods. Expression cultures were initiated with 10-200 freshly transformed colonies into 250 mL LB medium containing 50 µg/ml antibiotic and 75 µM IPTG (isopropyl-α-D-thiogalatopyranoside). The cultures were grown at 28° C. for 24 hours at 180-200 rpm. The cells were collected by centrifugation in 250 ml Nalgene bottles at 3,400×g for 10 minutes at 4 C. The pellets were suspended in 4-4.5 mL Butterfield's Phosphate solution (Hardy Diagnostics, Santa Maria, Calif.; 0.3 mM potassium phosphate pH 7.2). The suspended cells were transferred to 50 mL polypropylene screw cap centrifuge tubes with 1 mL of 0.1 mm diameter glass beads (Biospec, Bartlesville, Okla., catalog number 1107901). The cell-glass bead mixture was chilled on ice, then the cells were lysed by sonication with two 45 second bursts using a 2 mm probe with a Branson Sonifier 250 (Danbury Conn.) at an output of ~20, chilling completely between bursts. The lysates were transferred to 2 mL Eppendorf tubes and centrifuged 5 minutes at 16,000×g. The supernatants were collected and the protein concentration measured. Bio-Rad Protein Dye Assay Reagent was diluted 1:5 with $H_2O$ and 1 mL was added to 10 µL, of a 1:10 dilution of each sample and to bovine serum albumin (BSA) at concentrations of 5, 10, 15, 20 and 25 µg/mL. The samples were read on a spectrophotometer measuring the optical density at the wavelength of 595 nm in the Shimadzu UV160U spectrophotometer (Kyoto, JP). The amount of protein contained in each sample was calculated against the BSA standard curve and adjusted to between 3-6 mg/mL with phosphate buffer. Lysates were run on a SDS protein gel to visualize expressed protein.

4.2—Evaluation of Common Cloning Strains for Sensitivity to BASTA

Selected cell lines of *Escherichia coli* and *Agrobacterium tumefaciens* were inoculated on minimal media containing incrementally increasing concentrations of Glufosinate (BASTA). The cell lines; BL21—Star (DE3), Top10, DH5=, *Agrobacterium tumefaciens* C58, and *Agrobacterium tumefaciens* LBA4404s were initially grown up on complex media. The *Escherichia coli* strains were grown in LB and the *Agrobacterium tumefaciens* strains were grown in YEP. Five microliters of bacterial culture was inoculated and dispersed evenly onto minimal media plates containing various concentrations of glufosinate. The concentrations consisted of 0 µg/ml, 250 µg/ml, 500 µg/ml, 1000 µg/ml, 2000 µg/ml, and 4000 µg/ml of BASTA. In addition, the bacterial strains were inoculated onto a plate of complex media as a control—*Agrobacterium tumefaciens* strains were inoculated on YEP agar plates, and *Escherichia coli* strains were inoculated on LB agar plates. The plates containing the *Escherichia coli* strains were incubated at 37° C. for 24 hours. The plates containing the *Agrobacterium tumefaciens* strains were incubate at 25° C. for 48 hours. After the allotted incubation time the plates were observed for bacterial growth. Table 7 illustrates the capability of the various strains to grow on minimal media containing glufosinate. Only one strain BL21—Star (DE3) cell line was substantially inhibited by glufosinate.

TABLE 7

Variable bacterial strain response to glufosinate grown on minimal media

| | Complex Cntrl | Min. Cntrl | Min. 250 µg/ml BASTA | Min. 500 µg/ml BASTA | Min. 1000 µg/ml BASTA | Min. 2000 µg/ml BASTA | Min. 4000 µg/ml BASTA |
|---|---|---|---|---|---|---|---|
| *E.coli*-star BL21 (DE3) | +++ | +++ | -- | -- | -- | -- | -- |

TABLE 7-continued

Variable bacterial strain response to glufosinate grown on minimal media

|  | Complex Cntrl | Min. Cntrl | Min. 250 µg/ml BASTA | Min. 500 µg/ml BASTA | Min. 1000 µg/ml BASTA | Min. 2000 µg/ml BASTA | Min. 4000 µg/ml BASTA |
|---|---|---|---|---|---|---|---|
| *E.coli* DH5α | +++ | +++ | +++ | +++ | +++ | +++ | -- |
| *E.coli* Top10 | +++ | +++ | +++ | +++ | +++ | + | -- |
| *Agrobacterium* C58 | +++ | +++ | +++ | +++ | +++ | ++ | -- |
| *Agrobacterium* LBA4404s | +++ | +++ | +++ | +++ | ++ | + | -- |

*E.coli* was grown for 24 hrs @ 37° C. *Agrobacterium* was grown for 48 hrs @ 25° C. +++ = Heavy Lawn Growth//++ = Light lawn growth //+ = patchy lawn growth //-- = No Growth 4.3—Recombinant Expression of DSM-2 (v2) to Complement Cell Growth of *Escherichia coli* BL21—Star (DE3)

A pET28a(+) expression plasmid containing PAT (v3) was constructed as a positive control. PAT (v3) was cloned as an NcoI-SacI fragment into corresponding restriction sites of pDAB779. Positive clones containing the PAT (v3) gene fragment were verified via restriction enzyme digestion. This construct was labeled as pDAB4434.

The plasmids, pDAB4434, pDAB4412, and an empty pET vector (control) were transformed into *Escherichia coli* BL21—Star (DE3) bacterial cells. Expression cultures were initiated with 10-200 freshly transformed colonies into 250 mL LB medium containing 50 µg/ml antibiotic and 75 µM IPTG (isopropyl-α-D-thiogalatopyranoside). The cultures were grown at 28° C. for 24 hours at 180-200 rpm. Five microliters of the culture was inoculated onto a complex media control and minimal media containing incrementally increasing concentrations of glufosinate and 20 µM IPTG. The cultures were dispersed evenly over the plates and incubated at 28° C. for 24 hours. After the allotted incubation time the plates were observed for bacterial growth. These results are illustrated in Table 8.

4.4—Use of Plant Promoters to Drive the Recombinant Expression of DSM-2 in *Escherichia coli* BL21—Star (DE3) Cells Plasmid constructs in which the DSM-2 (v2) and PAT gene coding sequences were expressed, under either the viral promoters CsVMV or the plant promoter AtUbi10, were assayed for complementation on minimal media containing glufosinate. The plasmids 3778 (Rb7 MARv3//AtUbi10 promoter//DSM-2 (v2)//Atu Orf 1 3'UTR), 3779 (Rb7 MARv3//AtUbi10 promoter//PAT//Atu Orf 1 3'UTR), 3264 (CsVMV promoter//DSM-2//Atu Orf24 3'UTR), 3037 (CsVMV promoter//PAT//Atu Orf 25/26 3'UTR), and 770 (control plasmid containing CsVMV promoter//GUS v3// Atu Orf 24 3'UTR) were transformed into *Escherichia coli* BL21—Star (DE3) and grown up in complex media. Five microliters of the cultures were plated on minimal media containing increasing concentrations of Glufosinate and incubated at 37° C. for 48 hours. The results are illustrated in Table 9. These data indicate that plant and viral promoters have moderate levels of functionality within bacterial cells and may be used to drive the expression of a selectable marker.

TABLE 8

|  | Complex Cntrl | Min. Cntrl | Min. 250 µg/ml BASTA | Min. 500 µg/ml BASTA | Min. 1000 µg/ml BASTA | Min. 2000 µg/ml BASTA | Min. 4000 µg/ml BASTA |
|---|---|---|---|---|---|---|---|
| Cntrl | +++ | +++ | -- | -- | -- | -- | -- |
| PAT | +++ | +++ | +++ | +++ | +++ | +++ | +++ |
| DSM2 | +++ | +++ | +++ | +++ | +++ | +++ | +++ |

*E. coli* was grown for 24 hrs @ 28° C. on media with 20 uM IPTG. -- = No Growth//+++ = Distinct Colony Growth

TABLE 9

|  |  | Min. Cntrl | Min. 250 µg/ml BASTA | Min. 500 µg/ml BASTA | Min. 1000 µg/ml BASTA | Min. 2000 µg/ml BASTA | Min. 4000 µg/ml BASTA |
|---|---|---|---|---|---|---|---|
| AtUbi10 Promoter | DSM-2-3778 | ++++ | ++++ | +++ | +++ | ++ | ++ |
|  | PAT-3779 | ++++ | ++++ | +++ | +++ | +++ | +++ |
|  | AHAS-4433 | ++++ | (+) | -- | -- | -- | -- |
| CsVMV Promoter | DSM-2 3264 | ++++ | ++ | + | -- | -- | -- |
|  | PAT-3037 | ++++ | ++ | + | -- | -- | -- |

TABLE 9-continued

|  | Min. Cntrl | Min. 250 µg/ml BASTA | Min. 500 µg/ml BASTA | Min. 1000 µg/ml BASTA | Min. 2000 µg/ml BASTA | Min. 4000 µg/ml BASTA |
|---|---|---|---|---|---|---|
| GUS-770 | ++++ | (+) | -- | -- | -- | -- |
| BL21 Cntrl | ++++ | (+) | -- | -- | -- | -- |

E.coli was grown for 48 hrs @ 37° C. ++++ = Heavy Lawn Growth; +++ = Lawn Growth, ++ = Lots of Distinct Colonies; + = Scattered Colony Growth.

Example 5—Purification of DSM-2 for Biological Characterization and Antibody Production for Western Analyses 5.1—Recombinant Expression.

E. coli BL-21 (DE3) Star cells (purchased from Invitrogen, Carlsbad, Calif.) harboring codon-optimized DSM-2 (v2) gene, in plasmid pDAB4412 was used to inoculate a 3 ml LB media supplemented with 50 µg/ml Kanamycin at 37° C. overnight for seed preparation. Approximately 2 ml of seed culture was transferred into a 1 L fresh LB containing Kanamycin (50 µg/ml) in a 2.8 L baffled Erlenmeyer flask. The cultures were incubated at 37° C. on a shaker (New Brunswick Scientific, Model Innova 44) at 250 RPM for approximately 6 hrs to obtain $OD_{600}$ close to 0.8-1.0. Isopropyl β-D-1-thiogalactopyranoside (IPTG) was added to final 75 µM in the cultures and continued to incubate at 18° C. for overnight induction. Cells were harvested by centrifugation at 8,000 RPM at 4° C. for 15 min, and cell paste was stored at −80° C. or immediately processed for purification.

Approximately 5 g of wet weight E. coli cells from 1 L culture were thawed and resuspended in 300 ml of extraction buffer containing 20 mM Tris-HCl, pH 8.0 and 0.3 ml of Protease Inhibitor Cocktail (Sigma, cat # P8465), and disrupted on ice for 15 minutes by sonication. The lysate was centrifuged at 4° C. at 24,000 RPM for 20 min, and the supernatant was filtered through 0.8 µm and 0.45 µm membrane. All subsequent protein separations were performed using Pharmacia AKTA Explorer 100 and operated at 4° C. The filtrate was applied at 10 ml/min to a QXL Sepharose Fast Flow column (Pharmacia HiPrep 16/10, 20 ml bed size) equilibrated with 20 mM Tris-HCl, pH 8.0 buffer. The column was washed with this buffer until the eluate $OD_{280}$ returned to baseline, proteins were eluted with 0.5 L of linear gradient from 0 to 0.4 M NaCl at a flow rate of 5 ml/min, while 5 ml fractions were collected. Fractions containing DSM-2 as determined by SDS-PAGE with apparent 20 kDa band (the predicted DSM-2 molecular weight is 19.3 kDa), also corresponding to the Glufosinate converting activity were pooled. The sample was diluted with 4 volumes of 20 mM Tris-HCl, pH 7.5 buffer contains 5 mM DTT, 0.5% Triton X-100, 5% glycerol, and re-applied to a Mono Q column (Pharmacia 10/100 GL, 8 ml bed size) at 4 ml/min. Proteins were eluted with 0.1-0.3 M NaCl gradient in the same buffer. A major peak containing DSM-2 was pooled, and solid ammonium sulfate was added to final 1.0 M, and applied to a Phenyl Fast Flow column (Pharmacia HiTrap, 5 ml bed size) equilibrated in 1.0 M ammonium sulfate in 20 mM Tris-HCl, pH 7.5. This column was washed with the equilibrating buffer at 4 ml/min until the $OD_{280}$ of the eluate returned to baseline, then proteins were eluted within 50 min (3 ml/min) by a linear gradient from 1.0 M to 0 Ammonium sulfate in 20 mM Tris-HCl, pH 7.5, and 3 ml fractions were collected. The main peak fractions contain DSM-2 eluted at 75 mS/cm was pooled, and concentrated to approximately 3 mg/ml using MWCO 10 kDa membrane centrifugal filter device (Millipore). The sample was then applied to a Superdex 75 gel filtration column (Pharmacia XK 16/60, 110 ml bed size) with PBS buffer at a flow rate of 1 ml/min. Peak fractions containing pure DSM-2 were pooled and stored at −80° C. Protein concentration was determined by Bradford assay or total amino acid analysis using bovine serum albumin as standard. Activity of purified DSM-2 was measured based on a standard procedure for phosphinothricin acetyltransferase (PAT) assay. (Wehrmann et al 1996)

5.2—Antibody Production

Rabbit polyclonal antibody against DSM-2 was produced using the Rabbit Polyclonal Antibody—Standard Protocols provided by Invitrogen Antibody Services (South San Francisco, Calif., Cat # M0300). E. coli-expressed and purified DSM-2 (see previous section) was supplied as immunogen. Briefly, two New Zealand rabbits were injected subcutaneously (SQ) with 1 mg of DSM-2 protein emulsified with 0.25 mg Keyhole Limpet Hemocyanin and Incomplete Freund's Adjuvant (IFA). The rabbits were rested for 2 weeks and boosted SQ three times with 0.5 mg of DSM-2 protein emulsified in IFA with three weeks of rest period in between. Two weeks after the final boost, sera were collected from each rabbit and tested on direct ELISA for titer (data not shown). Two additional boosts and terminal bleed (Invitrogen Cat # M0311 and M0313) were conducted on rabbit number 2, which gave better titer on specific antibodies.

5.3—Western Blotting Analysis

Approximately 100 mg of calli tissue was put into a 2 mL microfuge tube containing 3 stainless steel BB beads. 250 µL of extraction buffer (phosphate buffered saline containing 0.1% Triton X-100, 10 mM DTT and 5 µL per mL protease inhibitors cocktail) was added and the tubes were secured in the Geno/Grinder (Model 2000-115, Certiprep, Metuchen, N.J.) and shaken for 6 min with setting at 1× of 500 rpm. Tubes were centrifuged at 10,000×g for 10 min and supernatant containing the soluble proteins was pipetted into separate tubes and stored in ice. The pellet was extracted a second time as described above and the supernatant was pooled with previous fraction and assayed.

Extracted proteins from plant samples were denatured in Laemmli Buffer and incubated at 95° C. for 10 min. Denatured proteins were separated on Novex 8-16% Tris-Glycine pre-cast gels (Invitrogen Cat # EC60452BOX) according to manufacturer's protocol, followed by transferring onto nitrocellulose membrane using standard protocol.

All Western blotting incubation steps were conducted at room temperature for one hour. The blot was first blocked in PBS containing 4% milk (PBSM) and then incubated in DSM-2-specific rabbit polyclonal antibody (see previous paragraph) diluted 5000-fold in PBSM. After three 5-min washes in PBS containing 0.05% Tween-20 (PBST), goat anti-rabbit antibody/horseradish peroxidase conjugate was incubated on the blot. Detected proteins were visualized using chemiluminescent substrate (Pierce Biotechnology, Rockford, Ill. Cat #32106) and exposure to X-ray film.

Example 6—Transformation into *Arabidopsis* and Selection 6.1—*Arabidopsis thaliana* Growth Conditions.

Wildtype *Arabidopsis* seed was suspended in a 0.1% Agarose (Sigma Chemical Co., St. Louis, Mo.) solution. The suspended seed was stored at 4° C. for 2 days to complete dormancy requirements and ensure synchronous seed germination (stratification).

Sunshine Mix LP5 (Sun Gro Horticulture, Bellevue, Wash.) was covered with fine vermiculite and sub-irrigated with Hoagland's solution until wet. The soil mix was allowed to drain for 24 hours. Stratified seed was sown onto the vermiculite and covered with humidity domes (KORD Products, Bramalea, Ontario, Canada) for 7 days.

Seeds were germinated and plants were grown in a Conviron (models CMP4030 and CMP3244, Controlled Environments Limited, Winnipeg, Manitoba, Canada) under long day conditions (16 hours light/8 hours dark) at a light intensity of 120-150 μmol/m$^2$ sec under constant temperature (22° C.) and humidity (40-50%). Plants were initially watered with Hoagland's solution and subsequently with deionized water to keep the soil moist but not wet.

6.2—*Agrobacterium* Transformation.

An LB+agar plate with erythromycin (Sigma Chemical Co., St. Louis, Mo.) (200 mg/L) or spectinomycin (100 mg/L) containing a streaked DH5α colony was used to provide a colony to inoculate 4 ml mini prep cultures (liquid LB+erythromycin). The cultures were incubated overnight at 37° C. with constant agitation. Qiagen (Valencia, Calif.) Spin Mini Preps, performed per manufacturer's instructions, were used to purify the plasmid DNA.

Electro-competent *Agrobacterium tumefaciens* (strains Z707s, EHA101s, and LBA4404s) cells were prepared using a protocol from Weigel and Glazebrook (2002). The competent *Agrobacterium* cells were transformed using an electroporation method adapted from Weigel and Glazebrook (2002). 50 μl of competent Agro cells were thawed on ice and 10-25 ng of the desired plasmid was added to the cells. The DNA and cell mix was added to pre-chilled electroporation cuvettes (2 mm). An Eppendorf Electroporator 2510 was used for the transformation with the following conditions, Voltage: 2.4 kV, Pulse length: 5 msec.

After electroporation, 1 ml of YEP broth (per liter: 10 g yeast extract, 10 g Bacto-peptone, 5 g NaCl) was added to the cuvette, and the cell-YEP suspension was transferred to a 15 ml culture tube. The cells were incubated at 28° C. in a water bath with constant agitation for 4 hours. After incubation, the culture was plated on YEP+agar with erythromycin (200 mg/L) or spectinomycin (100 mg/L) and streptomycin (Sigma Chemical Co., St. Louis, Mo.) (250 mg/L). The plates were incubated for 2-4 days at 28° C.

Colonies were selected and streaked onto fresh YEP+agar with erythromycin (200 mg/L) or spectinomycin (100 mg/L) and streptomycin (250 mg/L) plates and incubated at 28° C. for 1-3 days. Colonies were selected for PCR analysis to verify the presence of the gene insert by using vector specific primers. Qiagen Spin Mini Preps, performed per manufacturer's instructions, were used to purify the plasmid DNA from selected *Agrobacterium* colonies with the following exception: 4 ml aliquots of a 15 ml overnight mini prep culture (liquid YEP+erythromycin (200 mg/L) or spectinomycin (100 mg/L)) and streptomycin (250 mg/L)) were used for the DNA purification. An alternative to using Qiagen Spin Mini Prep DNA was lysing the transformed *Agrobacterium* cells, suspended in 10 μl of water, at 100° C. for 5 minutes. Plasmid DNA from the binary vector used in the *Agrobacterium* transformation was included as a control. The PCR reaction was completed using Taq DNA polymerase from Takara Mirus Bio Inc. (Madison, Wis.) per manufacturer's instructions at 0.5× concentrations. PCR reactions were carried out in a MI Research Peltier Thermal Cycler programmed with the following conditions; 1) 94° C. for 3 minutes, 2) 94° C. for 45 seconds, 3) 55° C. for 30 seconds, 4) 72° C. for 1 minute, for 29 cycles then 1 cycle of 72° C. for 10 minutes. The reaction was maintained at 4° C. after cycling. The amplification was analyzed by 1% agarose gel electrophoresis and visualized by ethidium bromide staining. A colony was selected whose PCR product was identical to the plasmid control.

6.3—*Arabidopsis* Transformation.

*Arabidopsis* was transformed using the floral dip method. The selected colony was used to inoculate one or more 15-30 ml pre-cultures of YEP broth containing erythromycin (200 mg/L) or spectinomycin (100 mg/L) and streptomycin (250 mg/L). The culture(s) was incubated overnight at 28° C. with constant agitation at 220 rpm. Each pre-culture was used to inoculate two 500 ml cultures of YEP broth containing erythromycin (200 mg/L) or spectinomycin (100 mg/L) and streptomycin (250 mg/L) and the cultures were incubated overnight at 28° C. with constant agitation. The cells were then pelleted at approx. 8700×g for 10 minutes at room temperature, and the resulting supernatant discarded. The cell pellet was gently resuspended in 500 ml infiltration media containing: ½× Murashige and Skoog salts/Gamborg's B5 vitamins, 10% (w/v) sucrose, 0.044 μM benzylamino purine (10 μl/liter of 1 mg/ml stock in DMSO) and 300 μl/liter Silwet L-77. Plants approximately 1 month old were dipped into the media for 15 seconds, being sure to submerge the newest inflorescence. The plants were then laid down on their sides and covered (transparent or opaque) for 24 hours, then washed with water, and placed upright. The plants were grown at 22° C., with a 16-hour light/8-hour dark photoperiod. Approximately 4 weeks after dipping, the seeds were harvested.

6.4—Selection of Transformed Plants.

Freshly harvested T$_1$ seed [DSM-2 (v2) gene] was allowed to dry for 7 days at room temperature. T$_1$ seed was sown in 26.5×51-cm germination trays (T.O. Plastics Inc., Clearwater, Minn.), each receiving a 200 mg aliquots of stratified T$_1$ seed (~10,000 seed) that had previously been suspended in 40 ml of 0.1% agarose solution and stored at 4° C. for 2 days to complete dormancy requirements and ensure synchronous seed germination.

Sunshine Mix LP5 (Sun Gro Horticulture Inc., Bellevue, Wash.) was covered with fine vermiculite and subirrigated with Hoagland's solution until wet, then allowed to gravity drain. Each 40 ml aliquot of stratified seed was sown evenly onto the vermiculite with a pipette and covered with humidity domes (KORD Products, Bramalea, Ontario, Canada) for 4-5 days. Domes were removed 1 day prior to initial transformant selection using 2,4-D postemergence spray (selecting for the co-transformed AAD-12 gene; see U.S. Ser. No. 60/731,044).

Seven days after planting (DAP) and again 11 DAP, T$_1$ plants (cotyledon and 2-4-lf stage, respectively) were sprayed with a 0.016% solution of 2,4-D herbicide (456 g ae/L 2,4-D Amine 4, Dow AgroSciences LLC, Indianapolis, Ind.) at a spray volume of 10 ml/tray (703 L/ha) using a DeVilbiss compressed air spray tip to deliver an effective rate of 50 g ae/ha 2,4-D DMA per application. Survivors (plants actively growing) were identified 4-7 days after the final spraying and transplanted individually into 3-inch pots prepared with potting media (Metro Mix 360). Transplanted plants were covered with humidity domes for 3-4 days and placed in a 22° C. growth chamber as before or moved to directly to the greenhouse. Domes were subsequently removed and plants reared in the greenhouse (22±5° C., 50±30% RH, 14 h light:10 dark, minimum 500 µE/m$^2$s$^1$ natural+supplemental light) at least 1 day prior to testing for the ability of DSM-2 (v2) to provide glufosinate herbicide resistance.

T$_1$ plants were then randomly assigned to various rates of glufosinate. For *Arabidopsis* 140 g ai/ha glufosinate is an effective dose to distinguish sensitive plants from ones with meaningful levels of resistance. Elevated rates were also applied to determine relative levels of resistance (280, 560, or 1120 g ai/ha). Table 10 shows comparisons drawn to an aryloxyalkanoate herbicide resistance gene (AAD-12 v1); see U.S. Ser. No. 60/731,044.

All glufosinate herbicide applications were applied by track sprayer in a 187 L/ha spray volume. The commercial Liberty™ formulation (200 g ai/L, Bayer Crop Science, Research Triangle Park, N.C.). T$_1$ plants that exhibited tolerance to glufosinate were further accessed in the T$_2$ generation.

6.5—Results of Selection of Transformed Plants.

The first *Arabidopsis* transformations were conducted using DSM-2 (v2) (plant optimized gene). T$_1$ transformants were first selected from the background of untransformed seed using a 2,4-D DMA selection scheme. Over 100,000 T$_1$ seed were screened and 260 2,4-D resistant plants (AAD-12 gene) were identified, equating to a transformation/selection frequency of 0.26% which is slightly higher than the normal range of selection frequency of constructs where AAD-12+ 2,4-D are used for selection. T$_1$ plants selected above were subsequently transplanted to individual pots and sprayed with various rates of commercial glufosinate herbicide. Table 10 compares the response of DSM-2 (v2) and control genes to impart glufosinate resistance to *Arabidopsis* T$_1$ transformants. Response is presented in terms of % visual injury 2 WAT. Data were presented as a histogram of individuals exhibiting little or no injury (<20%), moderate injury (20-40%), or severe injury (>40%). Since each T$_1$ is an independent transformation event, one can expect significant variation of individual T$_1$ responses within a given rate. An arithmetic mean and standard deviation is presented for each treatment. Untransformed-wildtype *Arabidopsis* served as a glufosinate sensitive control. The DSM-2 (v2) gene imparted herbicide resistance to individual T$_1$ *Arabidopsis* plants. Within a given treatment, the level of plant response varied greatly and can be attributed to the fact each plant represents an independent transformation event. Of important note, at above 140 g ai/ha glufosinate, there were individuals that were unaffected while some were severely affected. An overall population injury average by rate is presented in Table 10 simply to demonstrate the significant difference between the plants transformed with DSM-2 (v2) versus the wildtype or AAD-12+PAT-transformed controls. Many DSM-2 (v2) individuals survived 1,120 g ai/ha glufosinate with little or no injury.

TABLE 10

T1 DSM-2 v2 (plant optimized)-transformed T$_1$ *Arabidopsis* response to a range of glufosinate rates applied postemergence compared to Wildtype and T$_1$ AAD-12 + PAT plants.

| Averages | % Injury | | | % Injury | |
|---|---|---|---|---|---|
| | <20% | 20-40% | >40% | Ave | Std dev |
| DSM-2 (v2) gene + AAD-12 | | | | | |
| 0 g ai/ha glufosinate | 20 | 0 | 0 | 0.0 | 0.0 |
| 140 g ai/ha glufosinate | 20 | 0 | 0 | 0.0 | 0.0 |
| 280 g ai/ha glufosinate | 19 | 1 | 0 | 3.0 | 5.0 |
| 560 g ai/ha glufosinate | 19 | 0 | 1 | 6.0 | 22.0 |
| 1120 g ai/ha glufosinate | 17 | 1 | 2 | 13.0 | 19.0 |
| Wildtype control | | | | | |
| 0 g ai/ha glufosinate | 10 | 0 | 0 | 0.0 | 0.0 |
| 140 g ai/ha glufosinate | 0 | 0 | 10 | 98.0 | 5.0 |
| 280 g ai/ha glufosinate | 0 | 0 | 10 | 100.0 | 0.0 |
| 560 g ai/ha glufosinate | 0 | 0 | 10 | 100.0 | 0.0 |
| 1120 g ai/ha glufosinate | 0 | 0 | 10 | 100.0 | 0.0 |
| PAT gene + AAD-12 | | | | | |
| 0 g ai/ha glufosinate | 10 | 0 | 0 | 0.0 | 0.0 |
| 140 g ai/ha glufosinate | 10 | 0 | 0 | 0.0 | 0.0 |
| 280 g ai/ha glufosinate | 10 | 0 | 0 | 0.0 | 0.0 |
| 560 g ai/ha glufosinate | 10 | 0 | 0 | 0.0 | 0.0 |
| 1120 g ai/ha glufosinate | 10 | 0 | 0 | 3.0 | 3.0 |

6.6—DSM-2 (v2) as a Selectable Marker.

The ability to use DSM-2 (v2) as a selectable marker using glufosinate as the selection agent was analyzed with *Arabidopsis* transformed as described above. Approximately 100 T$_1$ generation *Arabidopsis* seed (100-150 seeds) containing for DSM-2 (v2) or 2 mg homozygous T$_5$ plants containing PAT were spiked into approximately 10,000 wildtype (sensitive) seed. Each tray of plants received two application timings of 280 g ai/ha glufosinate at the following treatment times: 7 DAP and 11 DAP. Treatments were applied with a DeVilbiss spray tip as previously described. Another 2 mg T$_1$ generation *Arabidopsis* seed from each was sown and not sprayed as a comparison count. Plants were identified as Resistant or Sensitive 17 DAP. Counts between treated and untreated were shown to be similar in Table 11. These results indicate DSM-2 (v2) can effectively be used as an alternative selectable marker for a population.

TABLE 11

Mass of seed sown and count of the number of plants that survived following a treatment of 280 g ai/ha glufosinate.

| Trt | Mass WT Planted | Mass PAT Planted | Mass DSM-2 (v2) Planted | Number of Surviving Plants Following glufosinate Spray |
|---|---|---|---|---|
| 1 | 200 mg | 0 mg | 0 mg | 0 |
| 2 | 0 mg | 2 mg | 0 mg | 154 |
| 3 | 200 mg | 2 mg | 0 mg | 121 |
| 4 | 0 mg | 0 mg | 2 mg | 117 |
| 5 | 200 mg | 0 mg | 2 mg | 121 |

6.7—Molecular Analysis:

6.7.1—Tissue Harvesting DNA Isolation and Quantification Xµl.

Fresh tissue is placed into tubes and lyophilized at 4° C. for 2 days. After the tissue is fully dried, a tungsten bead (Heavy Shot) is placed in the tube and the samples are subjected to 1 minute of dry grinding using a Kelco bead mill. The standard DNeasy DNA isolation procedure is then followed (Qiagen, DNeasy 69109). An aliquot of the extracted DNA is then stained with Pico Green (Molecular Probes P7589) and read in the fluorometer (Wavelength 485/530-BioTek) with known standards to obtain the concentration in ng/μl.

6.7.2—Invader Assay Analysis Xμl.

The DNA samples are diluted to 0.7 ng/μl then denatured by incubation in a thermocycler at 95° C. for 10 minutes. The Invader assay reaction mix is then prepared by following the 96 well format procedure published by Third Wave Technologies. 7.5 μl of the prepared reaction mix is dispersed into each well of the a 96 well plate followed by an aliquot of 7.5 μl of controls and 0.7 ng/μl diluted, denatured unknown samples. Each well is overlaid with 15 μl of mineral oil (Sigma). The plates are then incubated at 63° C. for 1 hour and read on the fluorometer (Biotek). Calculation of % signal over background for the target probe (FAM dye wavelength 560/620) divided by the % signal over background internal control probe (RED dye wavelength 485/530) will calculate the ratio. The ratio was then used to determine the event's zygosity.

6.8—Heritability.

A variety of $T_1$ events were self-pollinated to produce $T_2$ seed. These seed were progeny tested by applying glufosinate (200 g ai/ha) to 100 random $T_2$ siblings. Each individual $T_2$ plant was transplanted to 3-inch square pots prior to spray application (track sprayer at 187 L/ha applications rate). Sixty-three percent of the $T_1$ families ($T_2$ plants) segregated in the anticipated 3 Resistant:1 Sensitive model for a dominantly inherited single locus with Mendelian inheritance as determined by Chi square analysis (P>0.05).

Invader for zygosity was performed on 16 randomly selected plants from each of the lines that segregated as a single locus. Seed were collected from homozygous invader determined $T_2$ individuals ($T_3$ seed). Twenty-five $T_3$ siblings from each of 4 homozygous invader determined $T_2$ families were progeny tested as previously described. All of the $T_2$ families that were anticipated to be homozygous (non-segregating populations) were non-segregating. These data show DSM-2 (v2) is stably integrated and inherited in a Mendelian fashion to at least three generations.

Example 7—Whiskers-Mediated Transformation of Corn Using Herbiace 7.1—Cloning of DSM-2 (v2).

The DSM-2 (v2) gene was cut out of the DASPICO45 vector as a Bbs1/Sac1 fragment. This was ligated directionally into the similarly cut pDAB3812 vector containing the ZmUbi1 monocot promoter. The two fragments were ligated together using T4 DNA ligase and transformed into DH5α cells. Minipreps were performed on the resulting colonies using Qiagen's QIASpin mini prep kit, and the colonies were digested to check for orientation. The final construct was designated pDAB3250, which contains ZmUbi1/DSM-2 (v2)/ZmPer5. An identical control vector containing the PAT gene was built as above. This construct was designated pDAB3251.

7.2—Callus/Suspension Initiation.

To obtain immature embryos for callus culture initiation, $F_1$ crosses between greenhouse-grown Hi-II parents A and B (Armstrong et al. 1991) were performed. When embryos were 1.0-1.2 mm in size (approximately 9-10 days post-pollination), ears were harvested and surface sterilized by scrubbing with Liqui-Nox® soap, immersed in 70% ethanol for 2-3 minutes, then immersed in 20% commercial bleach (0.1% sodium hypochlorite) for 30 minutes.

Ears were rinsed in sterile, distilled water, and immature zygotic embryos were aseptically excised and cultured on 15Ag10 medium (N6 Medium (Chu et al., 1975), 1.0 mg/L 2,4-D, 20 g/L sucrose, 100 mg/L casein hydrolysate (enzymatic digest), 25 mM L-proline, 10 mg/L AgNO$_3$, 2.5 g/L Gelrite, pH 5.8) for 2-3 weeks with the scutellum facing away from the medium. Tissue showing the proper morphology (Welter et al., 1995) was selectively transferred at biweekly intervals onto fresh 15Ag10 medium for about 6 weeks, then transferred to 4 medium (N6 Medium, 1.0 mg/L 2,4-D, 20 g/L sucrose, 100 mg/L casein hydrolysate (enzymatic digest), 6 mM L-proline, 2.5 g/L Gelrite, pH 5.8) at bi-weekly intervals for approximately 2 months.

To initiate embryogenic suspension cultures, approximately 3 ml packed cell volume (PCV) of callus tissue originating from a single embryo was added to approximately 30 ml of H9CP+ liquid medium (MS basal salt mixture (Murashige and Skoog, 1962), modified MS Vitamins containing 10-fold less nicotinic acid and 5-fold higher thiamine-HCl, 2.0 mg/L 2,4-D, 2.0 mg/L α-naphthaleneacetic acid (NAA), 30 g/L sucrose, 200 mg/L casein hydrolysate (acid digest), 100 mg/L myo-inositol, 6 mM L-proline, 5% v/v coconut water (added just before subculture), pH 6.0). Suspension cultures were maintained under dark conditions in 125 ml Erlenmeyer flasks in a temperature-controlled shaker set at 125 rpm at 28° C. Cell lines typically became established within 2 to 3 months after initiation. During establishment, suspensions were subcultured every 3.5 days by adding 3 ml PCV of cells and 7 ml of conditioned medium to 20 ml of fresh H9CP+ liquid medium using a wide-bore pipette. Once the tissue started doubling in growth, suspensions were scaled-up and maintained in 500 ml flasks whereby 12 ml PCV of cells and 28 ml conditioned medium was transferred into 80 ml H9CP+ medium. Once the suspensions were fully established, they were cryopreserved for future use.

7.3 Cryopreservation and Thawing of Suspensions.

Two days post-subculture, 4 ml PCV of suspension cells and 4 ml of conditioned medium were added to 8 ml of cryoprotectant (dissolved in H9CP+ medium without coconut water, 1 M glycerol, 1 M DMSO, 2 M sucrose, filter sterilized) and allowed to shake at 125 rpm at 4° C. for 1 hour in a 125 ml flask. After 1 hour 4.5 ml was added to a chilled 5.0 ml Corning cryo vial. Once filled individual vials were held for 15 minutes at 4° C. in a controlled rate freezer, then allowed to freeze at a rate of −0.5° C./minute until reaching a final temperature of −40° C. After reaching the final temperature, vials were transferred to boxes within racks inside a Cryoplus 4 storage unit (Forma Scientific) filled with liquid nitrogen vapors.

For thawing, vials were removed from the storage unit and placed in a closed dry ice container, then plunged into a water bath held at 40-45° C. until "boiling" subsided. When thawed, contents were poured over a stack of ~8 sterile 70 mm Whatman filter papers (No. 4) in covered 100×25 mm Petri dishes. Liquid was allowed to absorb into the filters for several minutes, then the top filter containing the cells was transferred onto GN6 medium (N6 medium, 2.0 mg/L 2,4-D, 30 g/L sucrose, 2.5 g/L Gelrite, pH 5.8) for 1 week. After 1 week, only tissue with promising morphology was transferred off the filter paper directly onto fresh GN6 medium. This tissue was subcultured every 7-14 days until 1 to 3 grams was available for suspension initiation into approximately 30 mL H9CP+ medium in 125 ml Erlenmeyer flasks. Three milliliters PCV was subcultured into fresh H9CP+ medium every 3.5 days until a total of 12 ml PCV was obtained, at which point subculture took place as described previously.

Approximately 24 hours prior to transformation, 12 ml PCV of previously cryopreserved embryogenic maize suspension cells plus 28 ml of conditioned medium was subcultured into 80 ml of GN6 liquid medium (GN6 medium lacking Gelrite) in a 500 ml Erlenmeyer flask, and placed on a shaker at 125 rpm at 28° C. This was repeated 2 times using the same cell line such that a total of 36 ml PCV was distributed across 3 flasks. After 24 hours the GN6 liquid media was removed and replaced with 72 ml GN6 S/M osmotic medium (N6 Medium, 2.0 mg/L 2,4-D, 30 g/L sucrose, 45.5 g/L sorbitol, 45.5 g/L mannitol, 100 mg/L myo-inositol, pH 6.0) per flask in order to plasmolyze the cells. The flasks were placed on a shaker in the dark for 30-35 minutes, and during this time a 50 mg/ml suspension of silicon carbide whiskers was prepared by adding the appropriate volume of GN6 S/M liquid medium to ~405 mg of pre-autoclaved, silicon carbide whiskers (Advanced Composite Materials, Inc.).

After incubation in GN6 S/M, the contents of each flask were pooled into a 250 ml centrifuge bottle. Once all cells settled to the bottom, all but ~14 ml of GN6 S/M liquid was drawn off and collected in a sterile 1-L flask for future use. The pre-wetted suspension of whiskers was vortexed for 60 seconds on maximum speed and 8.1 ml was added to the bottle, to which 170 μg DNA was added as a last step. The bottle was immediately placed in a modified Red Devil 5400 commercial paint mixer and agitated for 10 seconds. After agitation, the cocktail of cells, media, whiskers and DNA was added to the contents of the 1-L flask along with 125 ml fresh GN6 liquid medium to reduce the osmoticant. The cells were allowed to recover on a shaker for 2 hours before being filtered onto Whatman #4 filter paper (5.5 cm) using a glass cell collector unit that was connected to a house vacuum line.

Approximately 6 mL of dispersed suspension was pipetted onto the surface of the filter as the vacuum was drawn. Filters were placed onto 60×20 mm plates of GN6 medium. Plates were cultured for 1 week at 28° C. in a dark box.

After 1 week, 20 of the filter papers were transferred to 60×20 mm plates of GN6 (1 Herbiace), 20 of the filter papers were transferred to 60×20 mm plates of GN6 (2 Herbiace) and 20 of the filter papers were transferred to 60×20 mm plates of GN6 (4 Herbiace) medium (N6 Medium, 2.0 mg/L 2,4-D, 30 g/L sucrose, 100 mg/L myo-inositol, 1, 2, or 4 mg/L bialaphos (from Herbiace) and, 2.5 g/L Gelrite, pH 5.8) Plates were placed in boxes and cultured for an additional week.

After an additional week, all of the filter papers were transferred to the same concentrations of GN6+ Herbiace medium (1H, 2H and/or 4H) again. The plates were placed in boxes and cultured for an additional week.

Three weeks post-transformation, the tissue was embedded by scraping ½ of the cells on the plate into 3.0 mL of melted GN6 agarose medium (N6 medium, 2.0 mg/L 2,4-D, 30 g/L sucrose, 100 mg/L myo-inositol, 7 g/L Sea Plaque agarose, pH 5.8, autoclaved for only 10 minutes at 121° C.) containing either 1, 2, or 4 mg/L bialaphos from Herbiace. The tissue was broken up and the 3 mL of agarose and tissue were evenly poured onto the surface of a 100×15 mm plate of GN6 (1H, 2H or 4H), depending on the concentration that the cells were originally cultured on. This was repeated with the other ½ of the cells on each plate. Once embedded, plates were individually sealed with Nescofilm® or Parafilm M®, and then cultured for about 4 weeks at 28° C. in dark boxes.

7.4—Protocol for Plant Regeneration.

Putatively transformed isolates are typically first visible 5-8 weeks post-transformation. Any potential isolates are removed from the embedded plate and transferred to fresh selection medium of the same concentration in 60×20 mm plates. If sustained growth is evident after approximately 2 weeks, an event is deemed to be resistant. A subset of the resistant events are then submitted for molecular analysis.

Regeneration is initiated by transferring callus tissue to a cytokinin-based induction medium, 28 (1H), containing, (MS salts and vitamins, 30.0 g/L sucrose, 5 mg/L BAP, 0.25 mg/L 2,4-D, 1 mg/L bialaphos, 2.5 g/L Gelrite; pH 5.7,) Cells are allowed to grow in low light (13 $\mu Em^{-2}\, s^{-1}$) for one week, then higher light (40 $\mu Em^{-2}\, s^{-1}$) for another week, before being transferred to regeneration medium, 36 (1H), which is identical to 28 (1H) except that it lacks plant growth regulators. Small (3-5 cm) plantlets are removed and placed into 150×25-mm culture tubes containing selection-free SHGA medium (Schenk and Hildebrandt basal salts and vitamins, 1972; 1 g/L myo-inositol, 10 g/L sucrose, 2.0 g/L Gelrite, pH 5.8). Once plantlets developed a sufficient root and shoot system, they are transplanted to soil in the greenhouse.

7.5—Molecular Analysis: Maize Materials and Methods.

7.5.1—Tissue Harvesting DNA Isolation and Quantification.

Fresh tissue is placed into tubes and lyophilized at 4° C. for 2 days. After the tissue is fully dried, a tungsten bead (Valenite) is placed in the tube and the samples are subjected to 1 minute of dry grinding using a Kelco bead mill. The standard DNeasy DNA isolation procedure is then followed (Qiagen, DNeasy 69109). An aliquot of the extracted DNA is then stained with Pico Green (Molecular Probes P7589) and read in the fluorometer (BioTek) with known standards to obtain the concentration in ng/μl.

7.5.2—PAT Invader Assay Analysis.

The DNA samples are diluted to 20 ng/μl then denatured by incubation in a thermocycler at 95° C. for 10 minutes. Signal Probe mix is then prepared using the provided oligo mix and $MgCl_2$ (Third Wave Technologies). An aliquot of 7.5 μl is placed in each well of the Invader assay plate followed by an aliquot of 7.5 μl of controls, standards, and 20 ng/μl diluted unknown samples. Each well is overlaid with 15 μl of mineral oil (Sigma). The plates are then incubated at 63° C. for 1 hour and read on the fluorometer (Biotek). Calculation of % signal over background for the target probe divided by the % signal over background internal control probe will calculate the ratio. The ratio of known copy standards developed and validated with Southern blot analysis is used to identify the estimated copy of the unknown events.

7.5.3—Polymerase Chain Reaction for PAT.

A total of 100 ng of total DNA is used as the template. 20 mM of each primer is used with the Takara Ex Taq PCR Polymerase kit (Mires TAKRR001A). Primers for the PAT PTU are (Forward MAS 123-GAACAGTTAGACATG-GTCTAAAGG) (SEQ ID NO:5) and (Reverse PerS-4-GCT-GCAACACTGATAAATGCCAACTGG) (SEQ ID NO:6). The PCR reaction is carried out in the 9700 Geneamp thermocycler (Applied Biosystems), by subjecting the samples to 94° C. for 3 minutes and 35 cycles of 94° C. for 30 seconds, 62° C. for 30 seconds, and 72° C. for 3 minute and 15 seconds followed by 72° C. for 10 minutes. Primers for Coding Region PCR PAT are (Forward-ATGGCTCAT- GCTGCCCTCAGCC) (SEQ ID NO:7) and (Reverse-CGGGC AGGCCTAACTCCACCAA) (SEQ ID NO:8). The PCR reaction is carried out in the 9700 Geneamp thermocycler (Applied Biosystems), by subjecting the samples to 94° C. for 3 minutes and 35 cycles of 94° C. for 30 seconds, 65° C. for 30 seconds, and 72° C. for 1 minute and 45 seconds followed by 72° C. for 10 minutes. Primers for Coding Region PCR for DSM-2 are (Forward-ATGCCTGGAACTGCTGAGGTC) (SEQ ID NO:9) and (Reverse-TGAGCGATGCCAGCATAAGCT) (SEQ ID NO:10). The PCR reaction is carried out in the 9700 Geneamp thermocycler (Applied Biosystems), by subjecting the samples to 94° C. for 3 minutes and 35 cycles of 94° C. for 30 seconds, 65° C. for 30 seconds, and 72° C. for 45 seconds followed by 72° C. for 10 minutes. PCR products are analyzed by electrophoresis on a 1% agarose gel stained with EtBr.

7.5.4—Southern Blot Analysis.

Southern blot analysis is performed with total DNA obtained from Qiagen DNeasy kit. A total of 5 µg of total genomic DNA is subjected to an overnight digestion with NcoI and SwaI to obtain integration data. A digestion of 5 µg with restriction enzyme SspI was used to obtain the PTU data. After analyzing the SspI digestion data, restriction enzyme MfeI was used to digest all of the remaining samples because it appeared to be a better choice in enzyme. After the overnight digestion an aliquot of ~100 ngs is run on a 1% gel to ensure complete digestion. After this assurance the samples are run on a large 0.85% agarose gel overnight at 40 volts. The gel is then denatured in 0.2 M NaOH, 0.6 M NaCl for 30 minutes. The gel is then neutralized in 0.5 M Tris HCl, 1.5 M NaCl pH of 7.5 for 30 minutes. A gel apparatus containing 20×SSC is then set up to obtain a gravity gel to nylon membrane (Millipore INYC00010) transfer overnight. After the overnight transfer the membrane is then subjected to UV light via a crosslinker (Stratagene UV stratalinker 1800) at 120,000 microjoules. The membrane is then washed in 0.1% SDS, 0.1 SSC for 45 minutes. After the 45 minute wash, the membrane is baked for 3 hours at 80° C. and then stored at 4° C. until hybridization. The hybridization template fragment is prepared using coding region PCR using plasmid DNA. The product is run on a 1% agarose gel and excised and then gel extracted using the Qiagen (28706) gel extraction procedure. The membrane is then subjected to a pre-hybridization at 60° C. step for 1 hour in Perfect Hyb buffer (Sigma H7033). The Prime it RmT dCTP-labeling reaction (Stratagene 300392) procedure is used to develop the p32 based probe (Perkin Elmer). The probe is cleaned up using the Probe Quant. G50 columns (Amersham 27-5335-01). Two million counts CPM per ml of Hybridization buffer are used to hybridize the Southern blots overnight. After the overnight hybridization the blots are then subjected to two 20 minute washes at 65° C. in 0.1% SDS, 0.1 SSC. The blots are then exposed to film overnight, incubating at −80° C.

7.6—Results

Three whisker-mediated transformations of maize were performed with each of the 2 constructs (PAT and DSM-2) described earlier. From those collective experiments, 230 isolates were recovered. On media containing 1 and 2 mg/L bialaphos (from Herbiace), event recovery between PAT and DSM-2 was very similar, however, event recovery on media containing 4 mg/L bialaphos was higher for PAT than for DSM-2.

TABLE 12

| Construct | Gene of Interest | Overall Events Recovered Per Bottle | | |
|---|---|---|---|---|
| | | 1 Herbiace | 2 Herbiace | 4 Herbiace |
| pDAB3250 | DSM2 | 46 | 41 | 17 |
| pDAB3251 | PAT | 44 | 37 | 45 |

Forty-eight of the DSM-2 events selected upon 1 or 2 Herbiace were submitted for copy number analysis and presence of an intact plant transcription unit (PTU) via Southern blot. All 48 events contained at least one copy of the DSM-2 gene. A subset of results from the lower-copy events (3 or less) are presented below.

TABLE 13

| Sample # | Integration DSM2 Southern Blot | PTU DSM2 Southern Blot |
|---|---|---|
| 1941[1]-005 | 2 | larger than expected |
| 1941[1]-006 | 3 | yes |
| 1941[1]-008 | 1 | yes |
| 1941[1]-009 | 2 | yes |
| 1941[1]-021 | 2 | yes |
| 1941[1]-023 | 2 | yes |
| 1941[2]-012 | 2 | yes |
| 1941[2]-014 | 2 | yes |
| 1941[2]-016 | 3 | yes |
| 1941[2]-017 | 2 | yes |
| 1941[2]-029 | 2 | yes |
| 1941[4]-038 | 1 | yes |
| 1941[5]-044 | 2 | yes |
| 1941[5]-045 | 2 | yes |
| 1941[5]-047 | 3 | yes |

Forty-eight of the PAT events selected upon 1, 2, or 4 Herbiace were submitted for copy number estimate and presence of an intact plant transcription unit (PTU) via Invader Assay and PCR, respectively. All 48 events contained at least one copy of the PAT gene. A subset of results from the lower-copy events (3 or less) are presented below.

TABLE 14

| Plant ID | Copy # | PTU PCR |
|---|---|---|
| 1942[1]-001 | 1 | + |
| 1942[1]-007 | 3 | + |
| 1942[2]-017 | 2 | + |
| 1942[3]-018 | 1 | + |
| 1942[3]-021 | 1 | + |
| 1942[3]-022 | 1 | + |
| 1942[3]-024 | 3 | + |

Approximately 6-10 $T_0$ plants were regenerated from each of 15 DSM-2-containing events and 7-8 plants were regenerated from each of 7 PAT-containing events listed earlier in order to assess tolerance to Liberty.

Callus tissue samples from 31 different events together with an untransformed callus (negative control) were analyzed with Western Blotting experiment. All samples except the negative control had one band observed with relative molecular weight of 20 kDa to the marker. It agreed with the predicted size of the protein of 19.7 kDa. In addition, the band also has the same size as the standard, i.e. purified DSM-2 protein purified from E. coli. With 0.7 µg/mL of the standard on the gel and given an arbitrary score of 5 (+++++), the bands from different events were relatively graded and listed in the table below.

TABLE 15

| Count | Event # | Total Grams | Western Detection |
|---|---|---|---|
| 1 | 1941[1]-018 | 0.090 | ++ |
| 2 | 1941[1]-019 | 0.070 | ++++ |
| 3 | 1941[1]-020 | 0.080 | ++ |
| 4 | 1941[1]-021 | 0.060 | ++ |
| 5 | 1941[1]-022 | 0.070 | ++++ |
| 6 | 1941[1]-023 | 0.050 | + |
| 7 | 1941[1]-024 | 0.080 | ++ |
| 8 | 1941[1]-025 | 0.050 | ++ |
| 9 | 1941[1]-026 | 0.070 | + |
| 10 | 1941[1]-027 | 0.060 | ++ |
| 11 | 1941[2]-028 | 0.080 | ++++ |
| 12 | 1941[2]-029 | 0.090 | +++ |
| 13 | 1941[2]-030 | 0.110 | ++ |
| 14 | 1941[2]-031 | 0.140 | +++ |
| 15 | 1941[2]-032 | 0.130 | +++ |
| 16 | 1941[2]-033 | 0.120 | +++ |
| 17 | 1941[2]-034 | 0.070 | +++ |
| 18 | 1941[2]-035 | 0.140 | + |
| 19 | 1941[4]-036 | 0.160 | + |
| 20 | 1941[4]-037 | 0.140 | ++ |
| 21 | 1941[4]-038 | 0.140 | +/− |
| 22 | 1941[4]-039 | 0.130 | + |
| 23 | 1941[4]-040 | 0.100 | +/− |
| 24 | 1941[4]-041 | 0.130 | ++ |
| 25 | 1941[4]-042 | 0.090 | +/− |
| 26 | 1941[4]-043 | 0.110 | + |
| 27 | 1941[5]-044 | 0.090 | +++ |
| 28 | 1941[5]-045 | 0.090 | ++ |
| 29 | 1941[5]-046 | 0.100 | +++ |
| 30 | 1941[5]-047 | 0.090 | +++ |
| 31 | 1941[5]-048 | 0.110 | + |

7.6.1—Leaf Paint Direct Comparison in $T_0$ Corn.

$T_0$ DSM-2 (v2) plants were painted with a rundown of glufosinate herbicide. Four siblings from each of 15 $T_0$ events were tested, and 4 leaves on each individual plant received a rundown of glufosinate at approximately V8 stage. Rundown treatments were randomized for each rate allowing for variation of treatment location on individual leaves. For corn, 0.25% v/v glufosinate is the minimum effective dose to distinguish sensitive plants from ones with meaningful levels of resistance. Elevated rates were also applied to determine relative levels of resistance (0.5%, 1.0%, and 2.0% v/v). Glufosinate treatments were applied using cotton tipped applicators to a treatment area of approximately 2.5 cm in diameter.

Table 16 compares the response of DSM-2 (v2) and control genes to impart glufosinate resistance to corn $T_0$ transformants. Response is presented in terms of % visual injury 2 WAT. Data are presented as a histogram of individuals exhibiting little or no injury (<20%), moderate injury (20-40%), or severe injury (>40%). Since each $T_0$ is an independent transformation event, one can expect significant variation of individual $T_0$ responses within a given rate. An arithmetic mean and standard deviation is presented for each treatment. Untransformed wildtype corn served as a glufosinate sensitive control. The DSM-2 (v2) gene imparted herbicide resistance to individual $T_0$ corn plants. Within a given treatment, the level of plant response varied greatly and can be attributed to the fact each plant represents an independent transformation event. Of important note, at up to 2% v/v glufosinate, DSM-2 (v2) performs better overall than PAT-transformed plants. An overall population injury average by rate is presented in Table 16 simply to demonstrate the significant difference between the plants transformed with DSM-2 (v2) versus the wildtype or PAT-transformed controls.

TABLE 16

$T_0$ DSM-2 (v2) (plant optimized)-transformed Corn plants response to a range of glufosinate rates applied as leaf paints to plants postemergence compared to Wildtype and $T_0$ PAT-transformed plants.

| Treatment | Wildtype % Injury | PAT % Injury | DSM-2(v2) % Injury |
|---|---|---|---|
| 2% v/v | 90 | 9 | 4 |
| 1% v/v | 84 | 6 | 2 |
| 0.5% v/v | 50 | 3 | 1 |
| 0.25% v/v | 33 | 1 | 0 |

7.6.2—Verification of High Glufosinate Tolerance in $T_2$ Corn.

The seed from the cross of $T_1$ DSM-2 (v2)×5XH751 were planted into 4-inch pots containing Metro Mix media and at 2 leaf stage were sprayed in the track sprayer set to 187 L/ha at 560 g ai/ha glufosinate to remove nulls. At 7 DAT nulls were removed and resistant plants were sprayed in the track sprayer as above at the following rates: 0, 560, 1120, 2240, and 4480 g ai/ha glufosinate. Plants were graded at 3 and 14 DAT and compared to 5XH751×Hi II control plants. Table 17 below shows that there are individual DSM-2 (v2) plants that provided up to 2240 g ai/ha glufosinate with less than 20% injury. DSM-2 (v2) also provided similar tolerance to 4480 g ai/ha glufosinate at the PAT transformed controls.

TABLE 17

$T_2$ Corn response to a range of glufosinate rates applied postemergence (14 DAT).

| | % Injury | | | % Injury | |
|---|---|---|---|---|---|
| Averages | <20% | 20-40% | >40% | Ave | Std dev |
| DSM-2 v2 (pDAS1941) | | | | | |
| Untreated control | 4 | 0 | 0 | 3 | 3 |
| 560 g ai/ha glufosinate | 4 | 0 | 0 | 6 | 3 |
| 1120 g ai/ha glufosinate | 2 | 2 | 0 | 18 | 6 |
| 2240 g ai/ha glufosinate | 1 | 3 | 0 | 21 | 5 |
| 4480 g ai/ha glufosinate | 0 | 4 | 0 | 29 | 5 |
| PAT (pDAS1942) | | | | | |
| Untreated control | 4 | 0 | 0 | 0 | 0 |
| 560 g ai/ha glufosinate | 4 | 0 | 0 | 6 | 5 |
| 1120 g ai/ha glufosinate | 0 | 1 | 3 | 25 | 10 |
| 2240 g ai/ha glufosinate | 2 | 1 | 1 | 25 | 12 |
| 4480 g ai/ha glufosinate | 0 | 3 | 1 | 33 | 5 |
| WT | | | | | |
| Untreated control | 4 | 0 | 0 | 3 | 3 |
| 560 g ai/ha glufosinate | 0 | 0 | 4 | 100 | 0 |
| 1120 g ai/ha glufosinate | 0 | 0 | 4 | 100 | 0 |
| 2240 g ai/ha glufosinate | 0 | 0 | 4 | 100 | 0 |
| 4480 g ai/ha glufosinate | 0 | 0 | 4 | 100 | 0 |

7.6.3—DSM-2 (v2) Heritability in Corn.

The seed from the cross of $T_1$ DSM-2 (v2)×5XH751 were planted into 3-inch pots containing Metro Mix media and at 2 leaf stage were sprayed in the track sprayer set to 187 L/ha at 0, 280, 560, 1120, 2240, and 4480 g ai/ha glufosinate. Plants were graded at 3 and 14 DAT and compared to 5XH751×Hi II control plants. Plants were graded as before with overall visual injury from 0-100%. To determine segregation of each population the rate of 1120 g ai/ha and higher was chosen. Resistant and sensitive plants were counted and it was determined that all of the $T_1$ families segregated as a single locus, dominant Mendelian trait (1R:1S) as determined by Chi square analysis. Surviving plants were selfed to produce the $T_2$ generation. DSM-2 (v2)

is heritable as a robust glufosinate resistance gene in multiple species when reciprocally crossed to a commercial hybrid.

A progeny test was also conducted on five DSM-2 (v2) $T_2$ families. The seeds were planted in three-inch pots as described above. At the 3 leaf stage all plants were sprayed with 560 g ai/ha glufosinate in the track sprayer as previously described. After 7 DAT, resistant and sensitive plants were counted. Four out of the five lines tested segregated as a single locus, dominant Mendelian trait (3R:1S) as determined by Chi square analysis.

7.6.4—Stacking of DSM-2(v2) to Increase Herbicide Spectrum

The cross of T1 plants with BE1146RR have been made. DSM-2(v2)-transformed plants can be conventionally bred to other corn lines containing additional traits of interest. An inbred (BE1146RR) containing the glyphosate tolerance trait CP4 was crossed with $T_1$ plants containing DSM-2(v2). Plants of the subsequent generation can be tested for efficacy of both herbicide tolerance traits by application of glufosinate and glyphosate in sequence or in tank mix at rates equal to or exceeding normally lethal herbicide rates (e.g. the plants could be sprayed with 280, 560, 1120 g ae/ha, or more, of both herbicides). This would identify the ability to use both herbicides in combination or sequential applications for herbicide resistance management.

Example 8—Protein Detection from Transformed Plants Via Antibody 8.1—Polyclonal Antibody Production.

Five milligrams purified DSM-2 (see previous section) was delivered to Invitrogen Custom Antibody Services (South San Francisco, Calif.) for rabbit polyclonal antibody production. The rabbit received 4 injections in the period of 12 weeks with each injection contained 0.5 mg of the purified protein suspended in 1 mL of Incomplete Freund's Adjuvant. Sera were tested in both direct-ELISA and Western blotting experiments to confirm specificity and affinity.

8.2—Extracting DSM-2 from Callus Tissue.

Four maize (Hi-II) leaf discs using a single-hole puncher were put into microfuge tubes containing 2 stainless steel beads (4.5 mm; Daisy Co., Cat #145462-000) and 500 µL plant extraction buffer (PBS containing 0.1% Triton X-100 and 5 µL per mL protease inhibitors cocktail (Sigma Cat # P9599). The tubes were secured in the Geno/Grinder (Model 2000-115, Certiprep, Metuchen, N.J.) and shook for 6 min with setting at 1× of 500 rpm. Tubes were centrifuged at 5000×g for 10 min and the supernatant containing the soluble proteins was assayed in Western Blotting experiments to detect the presence of DSM-2.

8.3—Western Blotting Analysis.

The leaf extract was spiked with various concentrations of purified DSM-2 and incubated with Laemmli sample buffer at 95° C. for 10 min followed by electrophoretic separation in 8-16% Tris-Glycine Precast gel. Proteins were then electro-transferred onto nitrocellulose membrane using standard protocol. After blocking in 4% skim milk in PBS, DSM-2 protein was detected by anti-DSM-2 antiserum followed by goat anti-rabbit/HRP conjugates. The detected protein was visualized by chemiluminescence substrate ECL Western Analysis Reagent (Amersham Cat. # RPN 21058).

8.4—Results.

Polyclonal antibodies for DSM-2 were generated using protein expressed in and purified from *E. coli* cells. After four injections, the antisera had high titer of anti-DSM-2 antibodies as observed in direct-ELISA. At 100,000-fold dilution, the serum still provided signal six times above background.

In Western blotting analysis (of DSM-2 in wild type maize (Hi-II) leaf matrix), the serum could detect a major band of approximately 22 kDa, which is comparable to the predicted molecular weight based on the DSM-2 (v2) gene. The same band could still be detected when the extract was spiked at 5 ng/mL, the lowest concentration tested. Minor bands were also observed at high DSM-2 concentrations, which are believed to be aggregate of the target protein as these were not observed at lower concentrations. A single major band with molecular weight comparable to the predicted one was observed. (The lanes run on this gel were a molecular weight marker, and leaf extracts containing DSM-2 protein at concentration 0.005, 0.05, 0.5 and 5 µg/mL, respectively.) In addition, the polyclonal antibody did not cross react to any maize leaf proteins as little background signal was observed.

Expression of DSM-2 from transformed Tobacco callus tissue was determined using Western blotting analysis. Detected band with comparative size as the standard (approx. 22 kDa) was observed in different events indicating that DSM-2 was expressed in transgenic tobacco tissue.

Example 9—Tobacco (Cell Culture) Transformation

Four days prior to transformation, a 1 week old NT-1 tobacco suspension, which was being subcultured every 7 days, was subcultured to fresh medium by adding 2 ml of the NT-1 culture or 1 ml of packed cells into 40 ml NT-1 B media. The subcultured suspension was maintained in the dark at 25±1° C. on a shaker at 125 rpm.

TABLE 18

NT-1 B medium recipe

| Reagent | Per liter |
|---|---|
| MS salts (10X) | 100 ml |
| MES | 0.5 g |
| Thiamine-HCl (1 mg/ml) | 1 ml |
| myo-inositol | 100 mg |
| $K_2HPO_4$ | 137.4 mg |
| 2,4-D (10 mg/ml) | 222 µl |
| Sucrose | 30 g |
| pH to 5.7 ± 0.03 | |

A 50% glycerol stock of *Agrobacterium tumefaciens* [strain LBA4404] harboring a binary vector of interest was used to initiate a liquid overnight culture by adding 20, 100, or 5000 to 30 ml YEP liquid (10 g/L yeast extract, 10 g/L Peptone, 5 g/L NaCl, 0-10 g/L Sucrose) containing 50-100 mg/L spectinomycin. The bacterial culture was incubated in the dark at 28° C. in an incubator shaker at 150-250 rpm until the $OD_{600}$ was 1.5±0.2. This took approximately 18-20 hrs.

For each vector tested, 20-70 mL of 4-day old suspension cells were transferred into a sterile vessel, to which 500-1750 µl of *Agrobacterium* suspension at the proper OD was added. To ensure a uniform mixture was achieved, the cells were pipetted up and down 5 times with a 10 ml wide-bore pipet. The uniform suspension was then drawn up into a 25 ml barrel of a repeat pipetter and 250 µl of the suspension was dispensed per well into 24-well plates, continuing until the suspension was exhausted. The well plates were wrapped in parafilm and cultured in the dark at 25±1° C. without shaking for a 3 day co-cultivation.

Following the co-cultivation, all excess liquid was removed from the individual wells with a 1 mL pipet tip, and remaining cells were resuspended in 1 ml NTC liquid (NT-1 B medium containing 500 mg/L carbenicillin, added after autoclaving). The contents of an individual well were dispersed across the entire surface of 100×25 mm selection plates using disposable transfer pipets. Selection media consisted of NTC media solidified with 8 g/l TC agar supplemented with 7.5 to 15 mg/L bialaphos or technical grade glufosinate ammonium, added after autoclaving. All selection plates, left unwrapped, were maintained in the dark at 28° C.

Putative transformants appeared as small clusters of callus on a background of dead, non-transformed cells. Calli were isolated approximately 2-6 weeks post-transformation. Each callus isolate was transferred to its own 60×20 mm plate containing the same selection medium and allowed to grow for approximately 2 weeks before being submitted for analysis.

9.1—Results

A side-by-side experiment comparing DSM-2 (v2) with PAT was completed. In the study, 100% of the PAT selection plates produced at least one PCR positive isolate on 10 mg/L bialaphos media, whereas 79% of the DSM-2 (v2) selection plates produced at least one PCR positive isolate. All events were assayed for the presence of the DSM-2 (v2) or PAT gene via coding region PCR, and were found to be positive.

TABLE 19

| Construct | Gene of Interest | Transformation Frequency on 10 mg/L Bialaphos following PCR Verification |
| --- | --- | --- |
| pDAB3778 | DSM-2 | 79% |
| pDAB3779 | PAT | 100% |

Western blots were performed on a small subset of the DSM-2 (v2)-selected events, and three positive events were identified as seen in the data below. In a second experiment, DSM-2 (v2)-treated tobacco cells were selected upon 7.5, 10, 12.5, or 15 mg/L bialaphos or technical grade glufosinate ammonium. Transformation frequencies (% of selection plates producing at least one callus) following verification by coding region PCR are listed in the table below.

TABLE 20

| Concentration in mg/L | Glufosinate | Bialaphos |
| --- | --- | --- |
| 7.5 | 55.6% | 38.9% |
| 10 | 50.0% | 44.4% |
| 12.5 | 44.4% | 38.9% |
| 15 | 38.9% | 22.2% |

Example 10—*Agrobacterium* Transformation of Other Crops

In light of the subject disclosure, additional crops can be transformed according to the subject invention using techniques that are known in the art. For *Agrobacterium*-mediated transformation of rye, see, e.g., Popelka and Altpeter (2003). For *Agrobacterium*-mediated transformation of soybean, see, e.g., Hinchee et al., 1988. For *Agrobacterium*-mediated transformation of sorghum, see, e.g., Zhao et al., 2000. For *Agrobacterium*-mediated transformation of barley, see, e.g., Tingay et al., 1997. For *Agrobacterium*-mediated transformation of wheat, see, e.g., Cheng et al., 1997. For *Agrobacterium*-mediated transformation of rice, see, e.g., Hiei et al., 1997.

The Latin names for these and other plants are given below. It should be clear that these and other (non-*Agrobacterium*) transformation techniques can be used to transform DSM-2 (v1), for example, into these and other plants, including but not limited to Maize (Gramineae *Zea mays*), Wheat (Pooideae *Triticum* spp.), Rice (Gramineae *Oryza* spp. and *Zizania* spp.), Barley (Pooideae *Hordeum* spp.), Cotton (*Abroma* Dicotyledoneae *Abroma augusta*, and Malvaceae *Gossypium* spp.), Soybean (Soya Leguminosae *Glycine max*), Sugar beet (Chenopodiaceae *Beta vulgaris altissima*), Sugar cane (*Arenga pinnata*), Tomato (Solanaceae *Lycopersicon esculentum* and other spp., *Physalis ixocarpa*, *Solanum incanum* and other spp., and *Cyphomandra betacea*), Potato, Sweet potato, Rye (Pooideae *Secale* spp.), Peppers (Solanaceae *Capsicum annuum*, *sinense*, and *frutescens*), Lettuce (Compositae *Lactuca sativa*, *perennis*, and *pulchella*), Cabbage, Celery (Umbelliferae *Apium graveolens*), Eggplant (Solanaceae *Solanum melongena*), Sorghum (all *Sorghum* species), Alfalfa (Leguminosae *Medicago sativum*), Carrot (Umbelliferae *Daucus carota sativa*), Beans (Leguminosae *Phaseolus* spp. and other genera), Oats (*Avena Sativa* and *Strigosa*), Peas (Leguminosae *Pisum*, *Vigna*, and *Tetragonolobus* spp.), Sunflower (Compositae *Helianthus annuus*), Squash (Dicotyledoneae *Cucurbita* spp.), Cucumber (Dicotyledoneae genera), Tobacco (Solanaceae *Nicotiana* spp.), Arabidopsis (Cruciferae *Arabidopsis thaliana*), Turfgrass (*Lolium*, *Agrostis*, and other families), and Clover (Leguminosae). Such plants, with DSM-2 (v2) genes, for example, are included in the subject invention. Vegetation control in plants endowed with glufosinate or bialaphos resistance as a result of transformation with DSM-2(v2) can be improved by selectively applying glufosinate.

DSM-2 (v2) has the potential to increase the applicability of herbicides, that can be inactivated by DSM-2.g, glufosinate, bialaphos, and/or phosphinothricin), for in-season use in many deciduous and evergreen timber cropping systems. Glufosinate or bialaphos-resistant timber species would increase the flexibility of over-the-top use of these herbicides without injury concerns. These species would include, but not limited to: alder, ash, aspen, beech, birch, cherry, eucalyptys, hickory, maple, oak, pine, and poplar. Use of glufosinate or bialaphos resistance for the selective control in ornamental species is also within the scope of this invention. Examples could include, but not be limited to, roses, Euonymus, petunia, begonia, and marigolds.

Example 11—DSM-2 (V2) Stacked with Glyphosate Tolerance Trait in any Crop

The vast majority of cotton, canola, and soybean acres planted in North America contain a glyphosate tolerance (GT) trait, and adoption of GT corn is on the rise. Additional GT crops (e.g., wheat, rice, sugar beet, and turf) have been under development but have not been commercially released to date. Many other glyphosate resistant species are in experimental to development stage (e.g., alfalfa, sugar cane, sunflower, beets, peas, carrot, cucumber, lettuce, onion, strawberry, tomato, and tobacco; forestry species like poplar and sweetgum; and horticultural species like marigold, petunia, and begonias; isb.vt.edu/cfdocs/fieldtestsl.cfm, 2005 on the World Wide Web). GTC's are valuable tools for the sheer breadth of weeds controlled and convenience and cost effectiveness provided by this system. However, glyphosate's utility as a now-standard base treatment is selecting for glyphosate resistant weeds. Furthermore, weeds that glyphosate is inherently less efficacious on are shifting to the predominant species in fields where glyphosate-only chemical programs are being practiced. By stacking DSM-2 (v2) with a GT trait, either through conventional breeding or jointly as a novel transformation event, weed control efficacy, flexibility, and ability to manage weed shifts and herbicide resistance development could be improved. Several scenarios for improved weed control options can be envisioned where DSM-2 (v2) and a GT trait are stacked in any monocot or dicot crop species:

a) Glyphosate can be applied at a standard postemergent application rate (420 to 2160 g ae/ha, preferably 560 to 840 g ae/ha) for the control of most grass and broadleaf weed species. For the control of glyphosate resistant broadleaf weeds like *Conyza canadensis* or weeds inherently difficult to control with glyphosate (e.g., *Commelina* spp, *Ipomoea* spp, etc), 280-2240 g ae/ha (preferably 350-1700 g ae/ha) glufosinate can be applied sequentially, tank mixed, or as a premix with glyphosate to provide effective control.

b) Currently, glyphosate rates applied in GTC's generally range from 560 to 2240 g ae/ha per application timing. Glyphosate is far more efficacious on grass species than broadleaf weed species. DSM-2 (v2)+GT stacked traits would allow grass-effective rates of glyphosate (105-840 g ae/ha, more preferably 210-420 g ae/ha). Glufosinate (at 280-2240 g ae/ha, more preferably 350-1700 g ae/ha) could then be applied sequentially, tank mixed, or as a premix with grass-effective rates of glyphosate to provide necessary broadleaf weed control.

One skilled in the art will recognize that other herbicides, (e.g. bialaphos) can be enabled by transformation of plants with DSM-2(v2). Specific rates can be determined by the herbicides labels compiled in the CPR (Crop Protection Reference) book or similar compilation, labels compiled online (e.g., cdms.net/manuf/manuf.asp), or any commercial or academic crop protection guides such as the Crop Protection Guide from Agriliance (2003). Each alternative herbicide enabled for use in HTCs by DSM-2 (v2), whether used alone, tank mixed, or sequentially, is considered within the scope of this invention.

Example 12—DSM-2 (V2) Stacked with AHAS Trait in any Crop

Imidazolinone herbicide tolerance (AHAS, et al.) is currently present in a number of crops planted in North America including, but not limited to, corn, rice, and wheat. Additional imidazolinone tolerant crops (e.g., cotton and sugar beet) have been under development but have not been commercially released to date. Many imidazolinone herbicides (e.g., imazamox, imazethapyr, imazaquin, and imazapic) are currently used selectively in various conventional crops. The use of imazethapyr, imazamox, and the non-selective imazapyr has been enabled through imidazolinone tolerance traits like AHAS et al. Commercial imidazolinone tolerant HTCs to date have the advantage of being non-transgenic. This chemistry class also has significant soil residual activity, thus being able to provide weed control extended beyond the application timing, unlike glyphosate or glufosinate-based systems. However, the spectrum of weeds controlled by imidazolinone herbicides is not as broad as glyphosate (Agriliance, 2003). Additionally, imidazolinone herbicides have a mode of action (inhibition of acetolactate synthase, ALS) to which many weeds have developed resistance (Heap, 2004). By stacking DSM-2 (v2) with an imidazolinone tolerance trait, either through conventional breeding or jointly as a novel transformation event, weed control efficacy, flexibility, and ability to manage weed shifts and herbicide resistance development could be improved. Several scenarios for improved weed control options can be envisioned where DSM-2 (v2) and an imidazolinone tolerance trait are stacked in any monocot or dicot crop species:

a) Imazethapyr can be applied at a standard postemergent application rate of (35 to 280 g ae/ha, preferably 70-140 g ae/ha) for the control of many grass and broadleaf weed species.
   i) ALS-inhibitor resistant broadleaf weeds like *Amaranthus rudis, Ambrosia trifida, Chenopodium album* (among others, Heap, 2004) could be controlled by tank mixing 280-2240 g ae/ha, more preferably 350-1700 g ae/ha glufosinate.
   ii) Inherently more tolerant broadleaf species to imidazolinone herbicides like *Ipomoea* spp. can also be controlled by tank mixing 280-2240 g ae/ha, more preferably 350-1700 g ae/ha glufosinate.

One skilled in the art of weed control will recognize that use of any of various commercial imidazolinone herbicides, and glufosinate based herbicides, alone or in multiple combinations, is enabled by DSM-2 (v2) transformation and stacking with any imidazolinone tolerance trait either by conventional breeding or genetic engineering. Specific rates of other herbicides representative of these chemistries can be determined by the herbicide labels compiled in the CPR (Crop Protection Reference) book or similar compilation, labels compiled online (e.g., cdms.net/manuf/manuf.asp), or any commercial or academic crop protection guides such as the Crop Protection Guide from Agriliance (2003). Each alternative herbicide enabled for use in HTCs by DSM-2 (v2), whether used alone, tank mixed, or sequentially, is considered within the scope of this invention.

Example 13—DSM-2 (V2) in Rice 13.1—Media Description.

Culture media employed were adjusted to pH 5.8 with 1 M KOH and solidified with 2.5 g/l Phytagel (Sigma). Embryogenic calli were cultured in 100×20 mm Petri dishes containing 40 ml semi-solid medium. Cell suspensions were maintained in 125-ml conical flasks containing 35 ml liquid medium and rotated at 125 rpm. Induction and maintenance of embryogenic cultures took place in the dark at 25-26° C. (Zhang et al. 1996).

Induction and maintenance of embryogenic callus took place on NB basal medium as described previously (Li et al. 1993), but adapted to contain 500 mg/l glutamine. Suspension cultures were initiated and maintained in SZ liquid medium (Zhang et al. 1998) with the inclusion of 30 g/l sucrose in place of maltose. Osmotic medium (NBO) consisted of NB medium with the addition of 0.256 M each of mannitol and sorbitol. Herbicide-resistant callus was selected on NB medium supplemented with 8 mg/l Bialaphos for 9 weeks with subculturing every 3 weeks.

13.2—Tissue Culture Development.

Mature desiccated seeds of *Oryza saliva* L. *japonica* cv. Taipei 309 were sterilized as described in Zhang et al. 1996. Embryogenic tissues were induced by culturing sterile mature rice seeds on NB medium in the dark. The primary callus approximately 1 mm in diameter, was removed from the scutellum and used to initiate cell suspension in SZ liquid medium. Suspensions were then maintained as described in Zhang 1995. Suspension-derived embryogenic tissues were removed from liquid culture 3-5 days after the previous subculture and placed on NBO osmotic medium to form a circle about 2.5 cm across in a Petri dish and cultured for 4 h prior to bombardment. Sixteen to 20 h after bombardment, tissues were transferred from NBO medium onto NBH8 herbiace selection medium, ensuring that the bombarded surface was facing upward, and incubated in the dark for 3 weeks. Newly formed callus was subcultured to fresh NBH8 medium twice every 3 weeks.

13.3—Microprojectile Bombardment.

All bombardments were conducted with the Biolistic PDS-1000/He™ system (Bio-Rad, Laboratories, Inc.). Three milligrams of 1.0 micron diameter gold particles were washed once with 100% ethanol, twice with sterile distilled water and resuspended in 50 µl water in a siliconized Eppendorf tube. Five micrograms plasmid DNA, 20 µl spermidine (0.1 M) and 50 µl calcium chloride (2.5 M) were added to the gold suspension. The mixture was incubated at room temperature for 10 min, pelleted at 10000 rpm for 10 s, resuspended in 60 µl cold 100% ethanol and 8-9 µl was distributed onto each macrocarrier. Tissue samples were bombarded at 1100 psi and 27 in of Hg vacuum as described by Zhang et al. (1996).

Example 14—DSM-2 (V2) Stacked with AAD-1 (V3) in any Crop

Glufosinate, like glyphosate, is a relatively non-selective, broad spectrum grass and broadleaf herbicide. Glufosinate's mode of action differs from glyphosate. It is faster acting, resulting in desiccation and "burning" of treated leaves 24-48 hours after herbicide application. This is advantageous for the appearance of rapid weed control. However, this also limits translocation of glufosinate to meristematic regions of target plants resulting in poorer weed control as evidenced by relative weed control performance ratings of the two compounds in many species (Agriliance, 2003).

By stacking AAD-1 (v3) (see U.S. Ser. No. 11/587,893; WO 2005/107437) with a glufosinate tolerance trait, either through conventional breeding or jointly as a novel transformation event, weed control efficacy, flexibility, and ability to manage weed shifts and herbicide resistance development could be improved. As mentioned in previous examples, by transforming crops with AAD-1 (v3), one can selectively apply AOPP herbicides in monocot crops, monocot crops will have a higher margin of phenoxy auxin safety, and phenoxy auxins can be selectively applied in dicot crops. Several scenarios for improved weed control options can be envisioned where AAD-1 (v3) and a glufosinate tolerance trait are stacked in any monocot or dicot crop species:
  a) Glufosinate can be applied at a standard postemergent application rate (200 to 1700 g ae/ha, preferably 350 to 500 g ae/ha) for the control of many grass and broadleaf weed species. To date, no glufosinate-resistant weeds have been confirmed; however, glufosinate has a greater number of weeds that are inherently more tolerant than does glyphosate.
    i) Inherently tolerant grass weed species (e.g., *Echinochloa* spp or *Sorghum* spp) could be controlled by tank mixing 10-200 g ae/ha (preferably 20-100 g ae/ha) quizalofop.
    ii) Inherently tolerant broadleaf weed species (e.g., *Cirsium arvensis* and *Apocynum cannabinum*) could be controlled by tank mixing 280-2240 g ae/ha, more preferably 560-2240 g ae/ha, 2,4-D for effective control of these more difficult-to-control perennial species and to improve the robustness of control on annual broadleaf weed species.
  b) A three-way combination of glufosinate (200-500 g ae/ha)+2,4-D (280-1120 g ae/ha)+quizalofop (10-100 g ae/ha), for example, could provide more robust, overlapping weed control spectrum. Additionally, the overlapping spectrum provides an additional mechanism for the management or delay of herbicide resistant weeds.

Example 15—DSM-2 (V2) Stacked with AAD-12 (V2) in any Crop

Glufosinate, like glyphosate, is a relatively non-selective, broad spectrum grass and broadleaf herbicide. Glufosinate's mode of action differs from glyphosate. It is faster acting, resulting in desiccation and "burning" of treated leaves 24-48 hours after herbicide application. This is advantageous for the appearance of rapid weed control. However, this also limits translocation of glufosinate to meristematic regions of target plants resulting in poorer weed control as evidenced by relative weed control performance ratings of the two compounds in many species (Agriliance, 2005).

By stacking AAD-12 (v1) with a glufosinate tolerance trait, either through conventional breeding or jointly as a novel transformation event, weed control efficacy, flexibility, and ability to manage weed shifts and herbicide resistance development could be improved. Several scenarios for improved weed control options can be envisioned where AAD-12 (v1) and a glufosinate tolerance trait are stacked in any monocot or dicot crop species:
  a) Glufosinate can be applied at a standard postemergent application rate (200 to 1700 g ac/ha, preferably 350 to 500 g ae/ha) for the control of many grass and broadleaf weed species. To date, no glufosinate-resistant weeds have been confirmed; however, glufosinate has a greater number of weeds that are inherently more tolerant than does glyphosate.
    i) Inherently tolerant broadleaf weed species (e.g., *Cirsium arvensis Apocynum cannabinum*, and *Conyza canadensis*) could be controlled by tank mixing 280-2240 g ae/ha, more preferably 560-2240 g ae/ha, 2,4-D for effective control of these more difficult-to-control perennial species and to improve the robustness of control on annual broadleaf weed species. Triclopyr and fluroxypyr would be acceptable components to consider in the weed control regimen. For triclopyr, application rates would typically range from 70-1120 g ae/ha, more typically 140-420 g ae/ha. For fluroxypyr, application rates would typically range from 35-560 g ae/ha, more typically 70-280 ae/ha.
  b) A multiple combination of glufosinate (200-500 g ae/ha)+/−2,4-D (280-1120 g ae/ha)+/−triclopyr or fluroxypyr (at rates listed above), for example, could provide more robust, overlapping weed control spectrum. Additionally, the overlapping spectrum provides an additional mechanism for the management or delay of herbicide resistant weeds.

Example 16—DSM-2 (V2) Stacked with Insect Resistance (IR) or Other Input Traits in any Crop Insect resistance in crops supplied by a transgenic trait is prevalent in corn and cotton production in North America and across the globe. Commercial products having combined IR and HT traits have been developed by multiple seed companies. These include Bt IR traits (e.g. Bt toxins listed at the website lifesci.sussex.ac.uk, 2006) and any or all of the HTC traits mentioned above. Thus, value this offering brings includes the ability to control multiple pest problems through genetic means in a single offering. The convenience of this offering will be restricted if weed control and insect control are accomplished independent of each other. DSM-2 (v2) alone or stacked with one or more additional HTC traits can be stacked with one or more additional input traits (e.g., insect resistance, fungal resistance, or stress tolerance, et al.) (isb.vt.edu/cfdocs/fieldtestsl.cfm, 2005) either through conventional breeding or jointly as a novel transformation event. Benefits include the convenience and flexibility described in Examples 11-15 above, together with the ability to manage insect pests and/or other agronomic stresses in addition to the improved weed control offered by DSM-2 (v2) and associated herbicide tolerance. Thus, the subject invention can be used to provide a complete agronomic package of improved crop quality with the ability to flexibly and cost effectively control any number of agronomic issues.

Combined traits of IR and HT have application in most agronomic and horticultural/ornamental crops and forestry. The combination of DSM-2 (v2) and its commensurate herbicide tolerance and insect resistance afforded by any of the number of Bt or non-Bt IR genes can be applied to the crop species listed (but not limited to) in Example 10. One skilled in the art of weed control will recognize that stacking DSM-2 with the corresponding HT trait or IR trait can be accomplished by conventional breeding or genetic engineering for example.

Example 17—Additional Gene Combinations

The subject invention also includes plants that produce one or more enzymes of the subject invention "stacked" together with one or more other herbicide resistance genes, including, but not limited to, glyphosate-, ALS-(imidazolinone, sulfonylurea), aryloxyalkanoate-, HPPD-, PPO-, and glufosinate-resistance genes, so as to provide herbicide-tolerant plants compatible with broader and more robust weed control and herbicide resistance management options. The present invention further includes methods and compositions utilizing homologues of the genes and proteins exemplified herein.

In some embodiments, the invention provides monocot and dicot plants tolerant to bialaphos, phosphinothricin, or glufosinate and one or more commercially available herbicides (e.g., glyphosate, glufosinate, paraquat, ALS-inhibitors (e.g., sulfonylureas, imidazolinones, triazolopyrimidine sulfonanilides, et al), HPPD inhibitors (e.g, mesotrione, isoxaflutole, et al.), 2,4-D, fluroxypyr, tricoplyr, dicamba, bromoxynil, aryloxyphenoxypropionates, and others). Vectors comprising nucleic acid sequences responsible for such herbicide tolerance are also disclosed, as are methods of using such tolerant plants and combinations of herbicides for weed control and prevention of weed population shifts. The subject invention enables novel combinations of herbicides to be used in new ways. Furthermore, the subject invention provides novel methods of preventing the development of, and controlling, strains of weeds that are resistant to one or more herbicides such as glyphosate. The subject invention enables novel uses of novel combinations of herbicides and crops, including preplant application to an area to be planted immediately prior to planting with seed for plants that would otherwise be sensitive to that herbicide (such as glufosinate).

The subject DSM-2 genes can be stacked with one or more pat/bar genes, for an additional mechanism for glufosinate tolerance, which are well known in the art.

For use of a gene, in plants, that encodes an HPPD (hydroxyl-phenyl pyruvate dioxygenases), see e.g. U.S. Pat. Nos. 6,268,549 and 7,297,541. Such "stacked" plants can be combined with other gene(s) for glufosinate resistance, and such stacked plants (and various other plants and stacked plants of the subject invention) can be used to prevent the development of glyphosate resistance.

Genes encoding enzymes with glyphosate N-acetyltransferase (GAT) activity can also be used (stacked) with DSM-2 gene(s) of the subject invention. See e.g. Castle et al. (2004), "Discovery of Directed Evolution of a Glyphosate Tolerance Gene," Science Vol. 34, pp. 1151-1154; and WO 2002/36782.

The subject DSM-2 genes can also be stacked with the AAD-1 and AAD-12, and AAD-13 genes of WO 2005/107437, WO 2007/053482, and U.S. Ser. No. 60/928,303, respectively, and can be used for combating glyphosate resistance in some preferred embodiments, as disclosed therein.

The invention claimed is:

1. A phosphinothricin-resistant transgenic plant cell comprising between 1 and 3 copies of the polynucleotide of SEQ ID NO:3 integrated in the genomic DNA of the plant cell, wherein the plant cell is resistant to glufosinate when applied at a rate of 560 g ai/ha.

2. A method of selecting for a transgenic plant cell, the method comprising:
   transforming a plurality of plant cells with a low copy number vector comprising a polynucleotide operably linked to a promoter operable in the plant cells, wherein the polynucleotide is SEQ ID NO:3, thereby producing transgenic plant cells comprising a low copy number of the polynucleotide; and
   growing the plurality of plant cells in a concentration of bialaphos or glufosinate that permits cells that express the polynucleotide to grow, while killing or inhibiting the growth of cells that do not express the polynucleotide,
   thereby selecting a transgenic plant cell that is resistant to glufosinate when applied at a rate of 560 g ai/ha.

3. The method of claim 2, wherein the method further comprises regenerating a plant from the transgenic plant cell.

4. A phosphinothricin-resistant plant comprising a plurality of the phosphinothricin-resistant transgenic plant cells of claim 1, wherein the plant is resistant to glufosinate when applied at a rate of 560 g ai/ha.

5. A seed of the plant of claim 4.

6. The phosphinothricin-resistant transgenic plant cell of claim 1, wherein the cell further comprises an insect-resistance gene derived from an organism selected from the group consisting of *Bacillus thruingiensis, Plotorhabdus*, and *Xenorhabdus*.

7. The phosphinothricin-resistant transgenic plant cell of claim 1, wherein the cell further comprises a second herbicide-resistance gene.

8. The phosphinothricin-resistant plant of claim 4, wherein the plant further comprises a herbicide resistance gene selected from the group consisting of AAD-1 and AAD-12, and wherein the plant is resistant to 2,4-D.

9. The phosphinothricin-resistant plant of claim 4, wherein the plant further comprises an insect-resistance gene from an organism selected from the group consisting of *Bacillus* thruingiensis, *Photorhabdus*, and *Xenorhabdus*.

10. The phosphinothricin-resistant plant of claim 4, wherein the plant further comprises a gene for an agronomic trait selected from the group consisting of fungal resistance, stress tolerance, increased yield, improved oil profile, improved fiber quality, viral resistance, delayed ripening, cold tolerance, and salt tolerance.

11. The phosphinothricin-resistant plant of claim 4, wherein the plant is soybean.

12. The phosphinothricin-resistant plant of claim 4, wherein the plant is corn.

13. The phosphinothricin-resistant transgenic plant cell of claim 1, wherein the plant cell comprises a single copy of the polynucleotide of SEQ ID NO:3 integrated in the genome of the plant cell.

14. The phosphinothricin-resistant plant of claim 4, wherein the plant is resistant to glufosinate when applied at a rate of 1,120 g ai/ha.

15. The phosphinothricin-resistant plant of claim 14, wherein the plant is soybean.

16. The phosphinothricin-resistant plant of claim 14, wherein the plant is corn.

* * * * *